US006592633B2

(12) United States Patent
Lang et al.

(10) Patent No.: US 6,592,633 B2
(45) Date of Patent: *Jul. 15, 2003

(54) DYE COMPOSITION FOR KERATIN FIBERS, WITH A CATIONIC DIRECT DYE AND A SUBSTANTIVE POLYMER

(75) Inventors: Gérard Lang, Saint Prix (FR); Jean Cotteret, Verneuil sur Seine (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 4 days.

(21) Appl. No.: 09/318,209

(22) Filed: May 25, 1999

(65) Prior Publication Data

US 2002/0007521 A1 Jan. 24, 2002

(30) Foreign Application Priority Data

May 25, 1998 (FR) .............................. 98 06549

(51) Int. Cl.$^7$ ................................. A61K 7/13
(52) U.S. Cl. ........................ 8/407; 8/409; 8/423; 8/426; 8/431; 8/553; 8/554; 8/555; 8/561; 8/562; 8/654; 8/655; 8/657; 8/659
(58) Field of Search ........................ 8/426, 407, 409, 8/423, 431, 553, 554, 555, 561, 562, 654, 655, 657, 659

(56) References Cited

U.S. PATENT DOCUMENTS

| 3,869,454 A | * | 3/1975 | Lang et al. ...................... 8/426 |
|---|---|---|---|
| 3,955,918 A | * | 5/1976 | Lang ............................... 8/426 |
| 3,985,499 A | | 10/1976 | Lang et al. ..................... 8/426 |
| 3,986,825 A | * | 10/1976 | Sokol ............................. 8/405 |
| 4,025,301 A | * | 5/1977 | Lang ............................... 8/426 |
| 4,157,388 A | | 6/1979 | Christiansen ............. 424/70.19 |
| 4,390,689 A | | 6/1983 | Jacquet et al. .............. 528/335 |
| 4,702,906 A | | 10/1987 | Jacquet et al. ........... 424/70.17 |
| 4,719,282 A | | 1/1988 | Nadolsky et al. .......... 528/310 |
| 4,772,462 A | * | 9/1988 | Boothe et al. ........... 424/70.22 |
| 4,781,723 A | * | 11/1988 | Gross et al. .................... 8/405 |
| 5,393,305 A | * | 2/1995 | Cohen et al. ................... 8/406 |
| 5,735,908 A | * | 4/1998 | Cotteret et al. ................. 8/410 |
| 5,879,412 A | * | 3/1999 | Rondeau et al. ............... 8/411 |
| 5,919,273 A | * | 7/1999 | Rondeau et al. ............... 8/412 |
| 5,948,124 A | * | 9/1999 | Grit ............................... 8/426 |
| 5,993,490 A | * | 11/1999 | Rondeau et al. ............... 8/409 |
| 6,001,135 A | * | 12/1999 | Rondeau et al. ............... 8/407 |
| 6,007,585 A | * | 12/1999 | Syed et al. ..................... 8/426 |

FOREIGN PATENT DOCUMENTS

| EP | 557203 | * | 8/1993 |
|---|---|---|---|
| FR | 2 140 205 | | 1/1973 |
| FR | 2 189 006 | | 1/1974 |
| FR | 2 270 846 | | 12/1975 |
| FR | 2 285 851 | | 4/1976 |
| FR | 2 586 913 | | 3/1987 |
| WO | 95/01772 | * | 1/1995 |
| WO | 95/15144 | * | 6/1995 |

OTHER PUBLICATIONS

Richard J. Crawford et al., "A replacement for Rubine dye for detecting cationics on keratin", Journal of the Society of Cosmetic Chemists, vol. 31, No. 5, Sep./Oct. 1980, pp. 273–278.
English language Derwent Abstract of FR 2 140 205, Jan. 1973.
English language Derwent Abstract of FR 2 189 006, Mar. 1974.
English language Derwent Abstract of FR 2 270 846, Jan. 1976.
English language Derwent Abstract of FR 2 285 851, May 1976.
English language Derwent Abstract of FR 2 586 913, Mar. 1987.
English language translation of EP 0 557 203.

* cited by examiner

*Primary Examiner*—Margaret Einsmann
(74) *Attorney, Agent, or Firm*—Finnegan, Henderson, Farabow, Garrett & Dunner LLP

(57) ABSTRACT

The invention relates to a dye composition for keratin fibers, in particular for human keratin fibers such as the hair, having, in a medium suitable for dyeing, at least one cationic direct dye of given formula, and containing at least one specific cationic or amphoteric substantive polymer.

The invention also relates to the dyeing processes and devices using the composition.

34 Claims, No Drawings

DYE COMPOSITION FOR KERATIN FIBERS, WITH A CATIONIC DIRECT DYE AND A SUBSTANTIVE POLYMER

The invention relates to a dye composition for keratin fibers, especially for human keratin fibers such as the hair, comprising, in a medium suitable for dyeing, at least one cationic direct dye of given formula, and at least one specific cationic or amphoteric substantive polymer.

The invention also relates to the dyeing processes and devices using said composition.

Two types of dyeing processes can be distinguished in the field of hair treatment. The first type of dyeing process is semi-permanent or temporary dyeing, or direct dyeing, which involves dyes capable of giving the hair's natural colour a more or less pronounced colour change that may withstand shampooing several times. These dyes are known as direct dyes; they can be used with or without an oxidizing agent. In the presence of an oxidizing agent, the aim is to obtain a lightening coloration. The lightening coloration is carried out by applying a mixture, prepared at the time of use, of a direct dye and an oxidizing agent to the hair. This mixture makes it possible to obtain, by lightening the melanin in the hair, an advantageous effect such as unifying the colour in the case of grey hair, or bringing out the colour in the case of naturally pigmented hair.

The second type of dyeing process is permanent dyeing or oxidation dyeing. This dyeing is carried out with dyes known as "oxidation" dyes comprising oxidation dye precursors and couplers. Oxidation dye precursors, commonly known as "oxidation bases," are initially colourless or weakly coloured compounds that develop their dyeing power on the hair in the presence of oxidizing agents added at the time of use, leading to the formation of coloured compounds and dyes. The formation of these coloured compounds and dyes results either from an oxidative condensation of the "oxidation bases" with themselves, or from an oxidative condensation of the "oxidation bases" with coloration modifier compounds commonly known as "couplers," which are generally present in the dye compositions used in oxidation dyeing.

To vary the shades obtained with the oxidation dyes, or to enrich them with glints, it is known to add direct dyes thereto.

Among the cationic direct dyes available in the field of dyeing keratin fibres, especially human keratin fibres, compounds which are already known are those whose structure is developed in the following text; nevertheless, these dyes have insufficient coloration properties, both with regard to the homogeneity of the colour distributed along the fibre ("unison"), where it is said that the coloration is too selective, and with regard to the staying power, or resistance to the various attacking factors to which the hair may be subjected (light, bad weather, shampooing).

After considerable research conducted in this field, the Applicants have now discovered that it is possible to obtain novel compositions for dyeing keratin fibres, which are capable of leading to less selective colorations and which are particularly resistant to the various attacking factors to which the hair may be subjected, by combining at least one specific cationic or amphoteric substantive polymer with at least one cationic direct dye known in the prior art and of formula (I) defined below.

This discovery forms the basis of the present invention.

Additional features and advantages of the invention are set forth in the description that follows, and, in part, will be apparent from the description or may be learned from the practice of the invention. The advantages of the invention will be realized and attained by the dyeing compositions, processes, and kits particularly pointed out in the written description and claims.

Both the foregoing general description and the following detailed description of the invention are exemplary and explanatory only and are not restrictive of the claimed invention.

A first subject of the present invention is, therefore, a composition for dyeing keratin fibres, especially human keratin fibres such as the hair, comprising, in a medium suitable for dyeing, (i) at least one cationic direct dye whose structure corresponds to formula (I) below, further comprising (ii) at least one specific cationic or amphoteric substantive polymer.

(i) The cationic direct dye which can be used according to the present invention is a compound of formula (I) below:

$$A-N=N-B \qquad (1)$$

in which: the symbol A represents a group selected from structures A1 to A3 below:

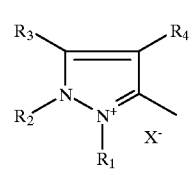

A1

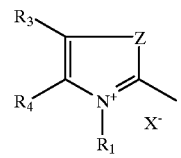

A2

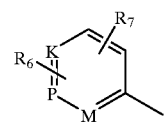

A3 in which structures A1 to A3, $R_1$ represents a $C_1$–$C_4$ alkyl radical, a phenyl radical which can be substituted with a $C_1$–$C_4$ alkyl radical or a halogen atom selected from chlorine, bromine, iodine and fluorine;

$R_2$ represents a $C_1$–$C_4$ alkyl radical or a phenyl radical;

$R_3$ and $R_4$, which may be identical or different, represent a $C_1$–$C_4$ alkyl radical, a phenyl radical or, in the case of structure A1, can together form a substituted benzene ring, and in the case of structure A2, can together form a benzene ring optionally substituted with one or more $C_1$–$C_4$ alkyl, $C_1$–$C_4$ alkoxy or $NO_2$ radicals;

$R_3$ can also represent a hydrogen atom;

Z represents an oxygen or sulphur atom or a group —$NR_2$;

M represents a group —CH, —CR (R denoting $C_1$–$C_4$ alkyl) or —$NR_5(X^-)_r$;

K represents a group —CH, —CR (R denoting $C_1$–$C_4$ alkyl) or —$NR_5(X^-)_r$;

P represents a group —CH, —CR (R denoting $C_1$–$C_4$ alkyl) or —$NR_5(X^-)_r$; r represents 0 or 1;

$R_5$ represents an atom $O^-$, a $C_1$–$C_4$ alkoxy radical or a $C_1$–$C_4$ alkyl radical;

$R_6$ and $R_7$, which may be identical or different, represent a hydrogen atom or a halogen atom selected from chlorine, bromine, iodine and fluorine, a $C_1$–$C_4$ alkyl or $C_1$–$C_4$ alkoxy radical or an —$NO_2$ radical;

$X^-$ represents an anion preferably selected from chloride, iodide, methyl sulphate, ethyl sulphate, acetate and perchlorate;

with the provisos that, if $R_4$ represents a $C_1$–$C_4$ alkyl radical and Z represents a sulphur atom, $R_3$ does not represent a hydrogen atom;

if $R_5$ represents $O^-$, then r represents zero;

if K or P or M represent $C_1$–$C_4$ —N-alkyl $X^-$, then $R_6$ or $R_7$ is other than a hydrogen atom;

if K represents —$NR_5(X^-)_r$, then M=P=—CH; —CR;

if M represents —$NR_5(X^-)_r$, then K=P=—CH; —CR;

if P represents —$NR_5(X^-)_r$, then K=M and represent —CH or —CR;

if Z represents —$NR_2$ and $R_2$ represents a $C_1$–$C_4$ alkyl radical, then at least one of the radicals $R_1$, $R_3$ or $R_4$ of $A_2$ is other than a $C_1$–$C_4$ alkyl radical;

the symbol B represents:

(a) a group of structure B1 below:

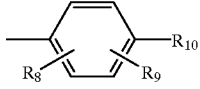

in which structure B1, $R_8$ represents a hydrogen atom, a halogen atom selected from chlorine, bromine, iodine and fluorine, a $C_1$–$C_4$ alkyl or $C_1$–$C_4$ alkoxy radical, a radical —OH, —$NO_2$, —$NHR_{11}$, —$NR_{12}R_{13}$ or —NHCO($C_1$–$C_4$)alkyl radical or forms, with $R_9$, a 5- or 6-membered ring which may or may not contain one or more hetero atoms selected from nitrogen, oxygen and sulphur;

$R_9$ represents a hydrogen atom, a halogen atom selected from chlorine, bromine, iodine and fluorine, or a $C_1$–$C_4$ alkyl or $C_1$–$C_4$ alkoxy radical, or forms, with $R_{10}$ or $R_{11}$, a 5- or 6-membered ring which may or may not contain one or more hetero atoms selected from nitrogen, oxygen and sulphur;

$R_{10}$ represents a hydrogen atom, an —OH radical, a radical —$NHR_{11}$ or a radical —$NR_{12}R_{13}$;

$R_{11}$ represents a hydrogen atom, a $C_1$–$C_4$ alkyl radical, a $C_1$–$C_4$ monohydroxyalkyl or $C_2$–$C_4$ polyhydroxyalkyl radical or a phenyl radical;

$R_{12}$ and $R_{13}$, which may be identical or different, represent a $C_1$–$C_4$ alkyl radical or a $C_1$–$C_4$ monohydroxyalkyl or $C_2$–$C_4$ polyhydroxyalkyl radical;

(b) a 5- or 6-membered nitrogenous heterocyclic group which can contain other hetero atoms and/or carbonyl groups and which can be substituted with one or more $C_1$–$C_4$ alkyl, amino or phenyl radicals, and in particular a group of structure B2 below:

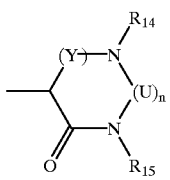

in which structure B2, $R_{14}$ and $R_{15}$, which may be identical or different, represent a hydrogen atom, a $C_1$–$C_4$ alkyl radical or a phenyl radical;

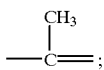

Y represents a —CO— radical or a radical n=0 or 1, where, when n represents 1, U represents a —CO— radical.

In the structures defined above, the $C_1$–$C_4$ alkyl or alkoxy group preferably represents methyl, ethyl, butyl, methoxy or ethoxy.

The cationic direct dyes of formula (I) which can be used in the dye compositions in accordance with the invention are known compounds and are described, for example, in patent applications FR-2,189,006, FR-2,285,851 and FR-2,140,205 and its Certificates of Addition, the disclosures of all of which are specifically incorporated by reference herein.

Among the cationic direct dyes of formula (I) which can be used in the dye compositions in accordance with the invention, those of formula (I) in which the symbol A represents structure A3 while the symbol B represents structure B1 or B2 are particularly preferred.

Among these compounds, preferred compounds include the compounds of structures $(I)_1$ to $(I)_{77}$ below:

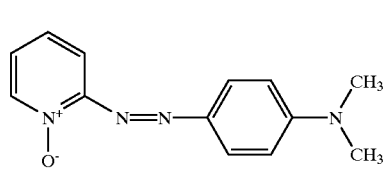

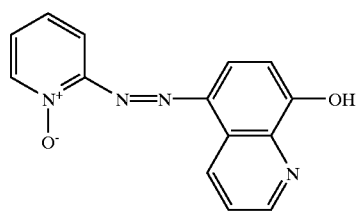

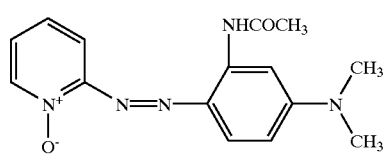

(I)4
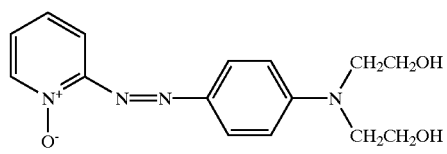
(I)5
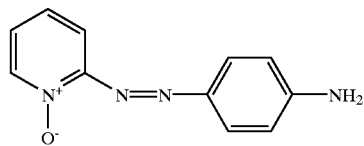
(I)6
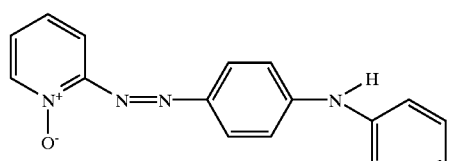
(I)7
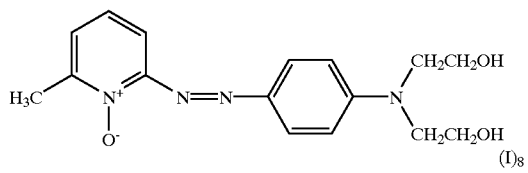
(I)8
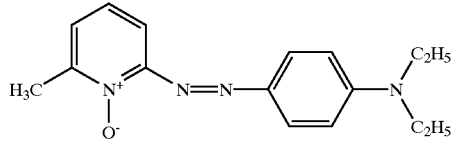
(I)9
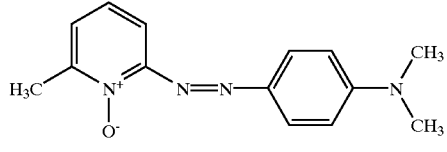
(I)10
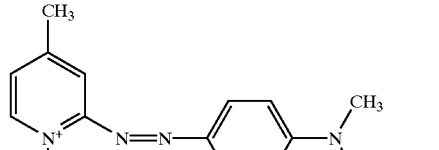
(I)11
(I)12
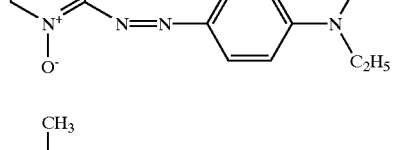
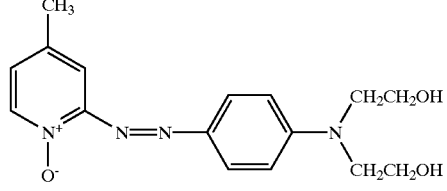
(I)13
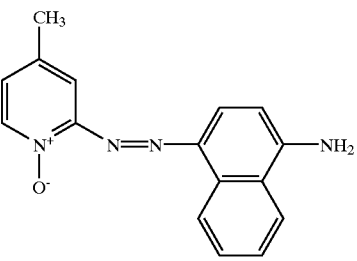
(I)14
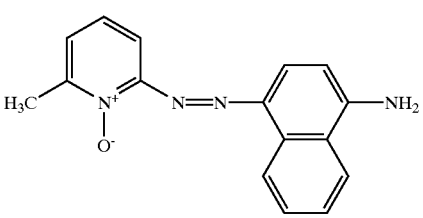
(I)15
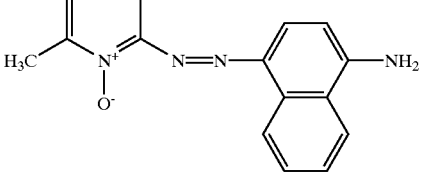
(I)16
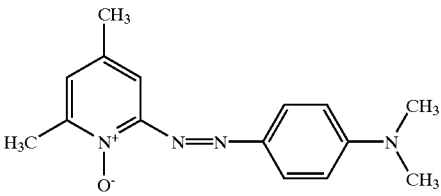
(I)17
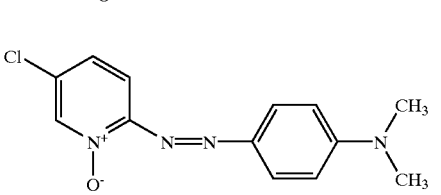
(I)18
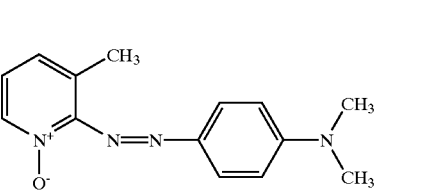
(I)19
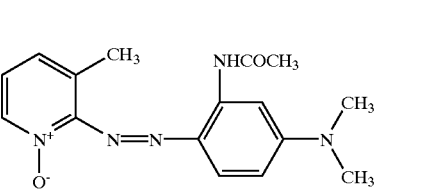
(I)20
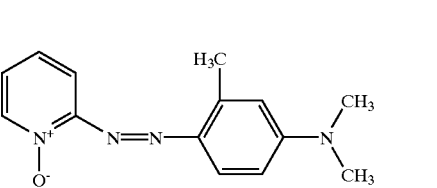

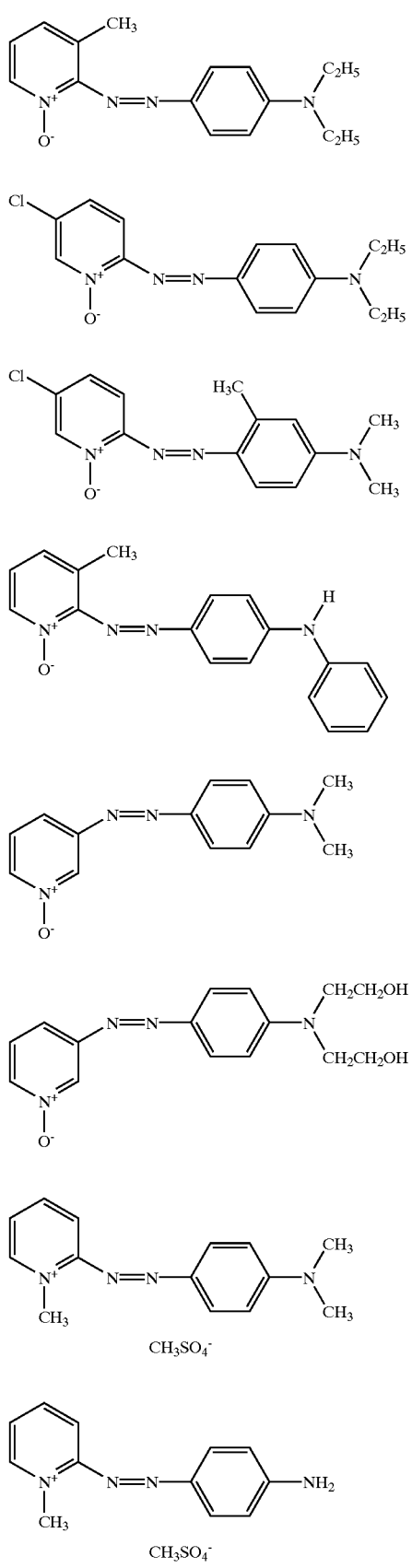
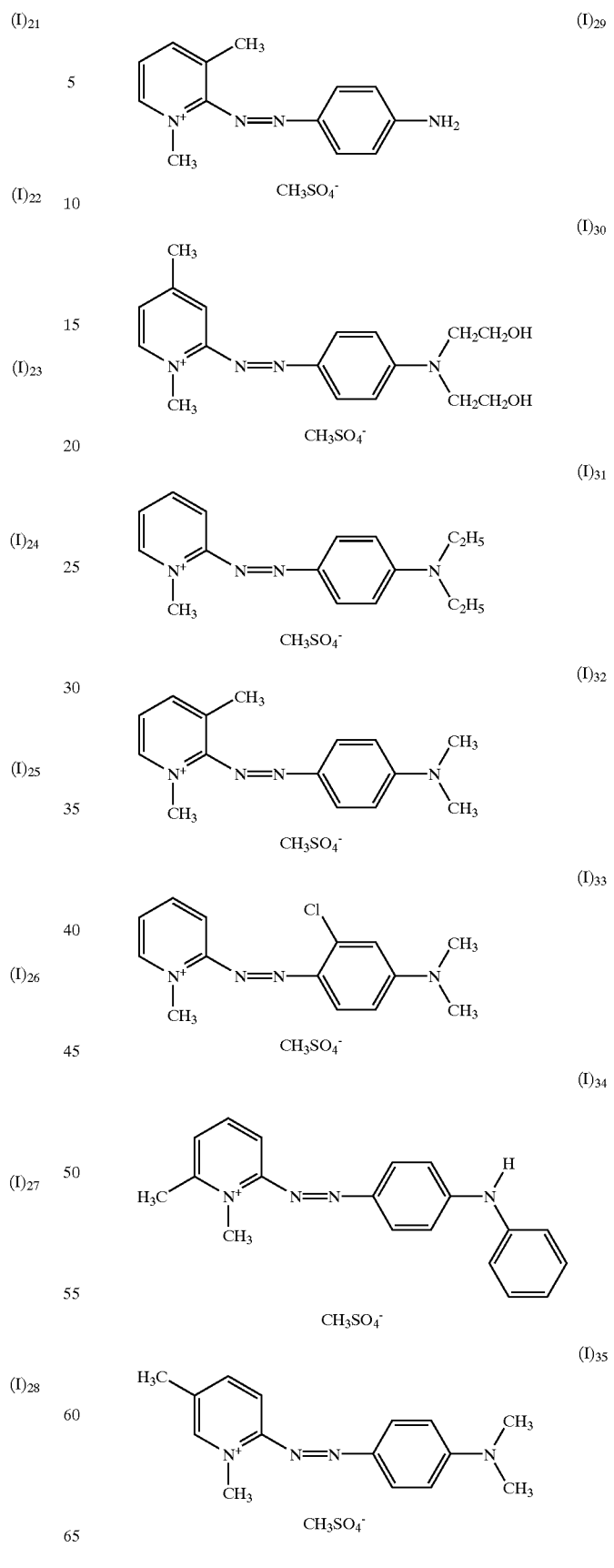

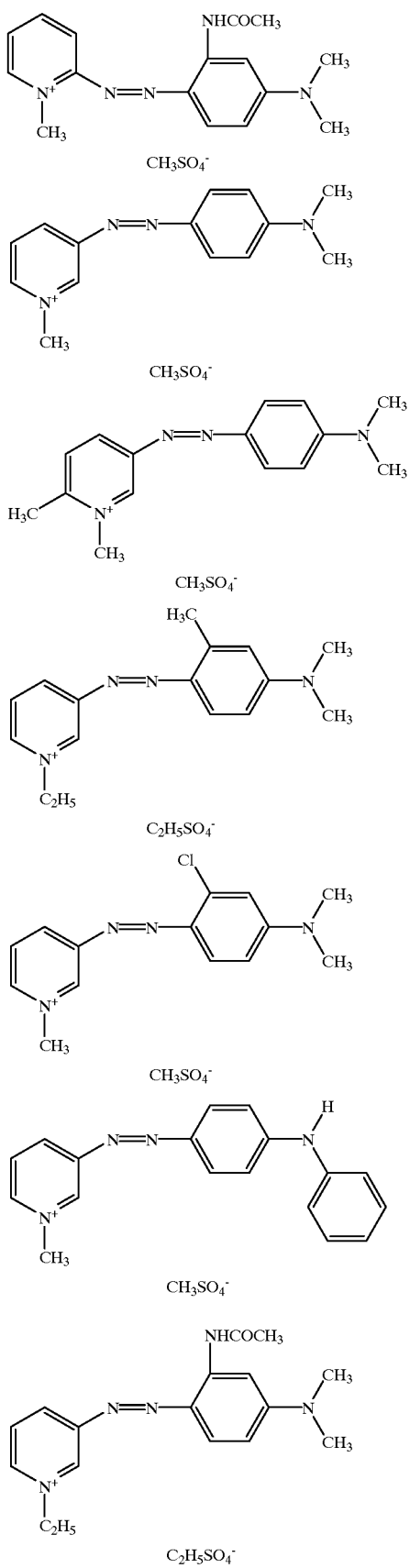
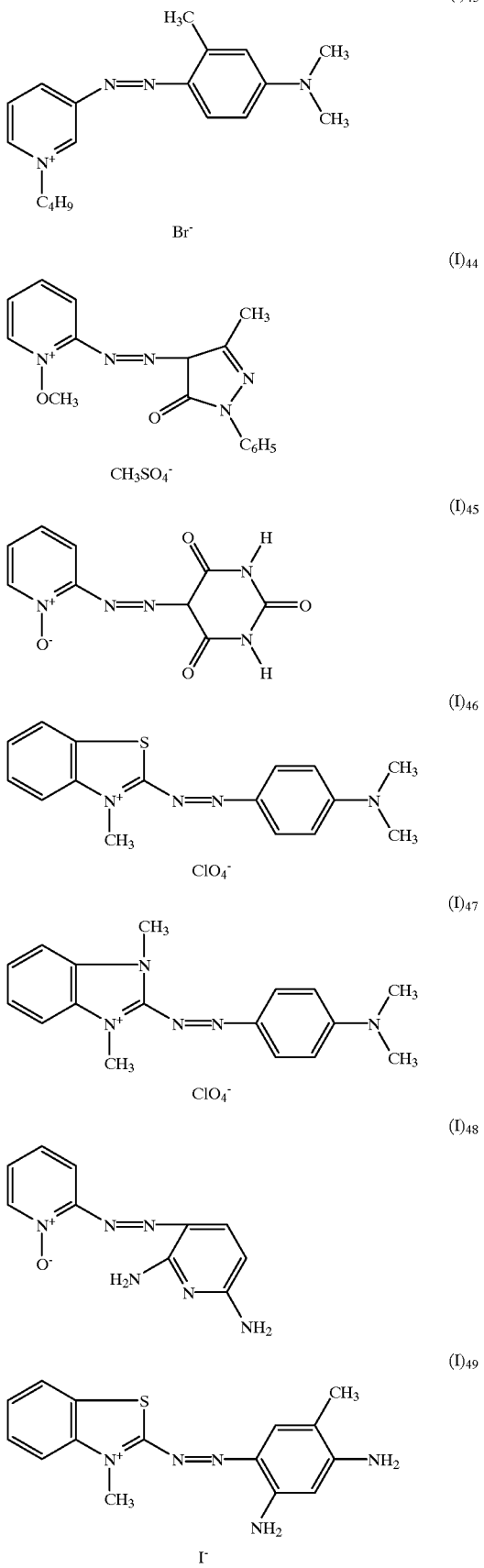

-continued
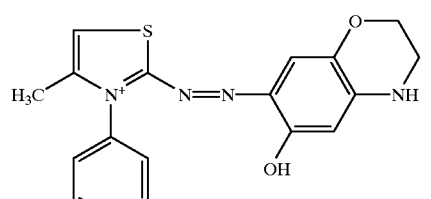
(I)₅₀
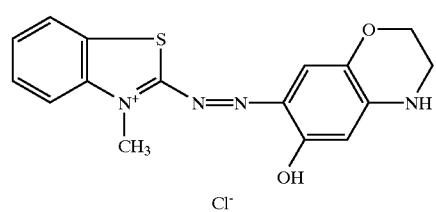
(I)₅₁
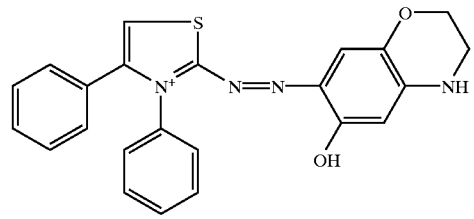
(I)₅₂
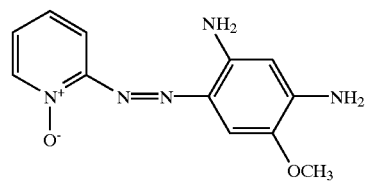
(I)₅₃
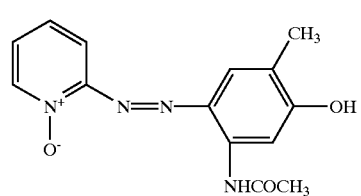
(I)₅₄
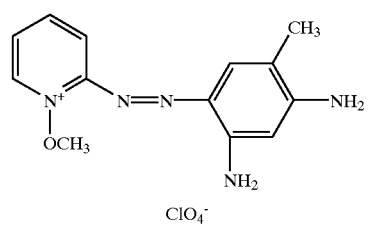
(I)₅₅
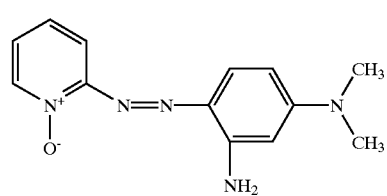
(I)₅₆
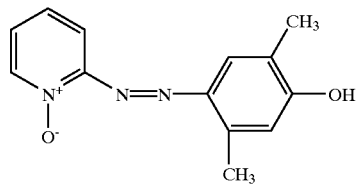
(I)₅₇
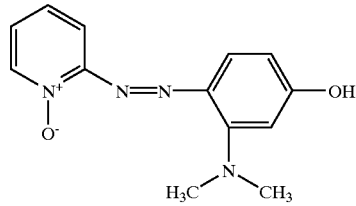
(I)₅₈
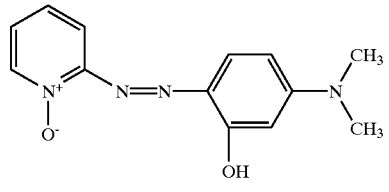
(I)₅₉
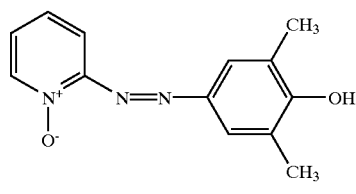
(I)₆₀
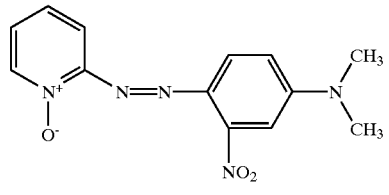
(I)₆₁
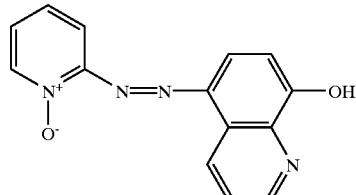
(I)₆₂
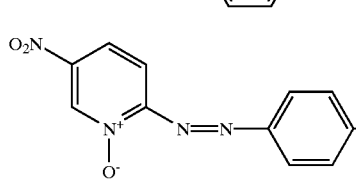
(I)₆₃
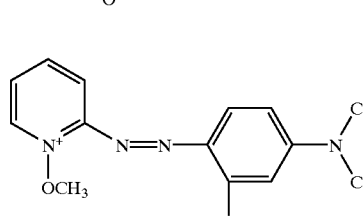
(I)₆₄

-continued

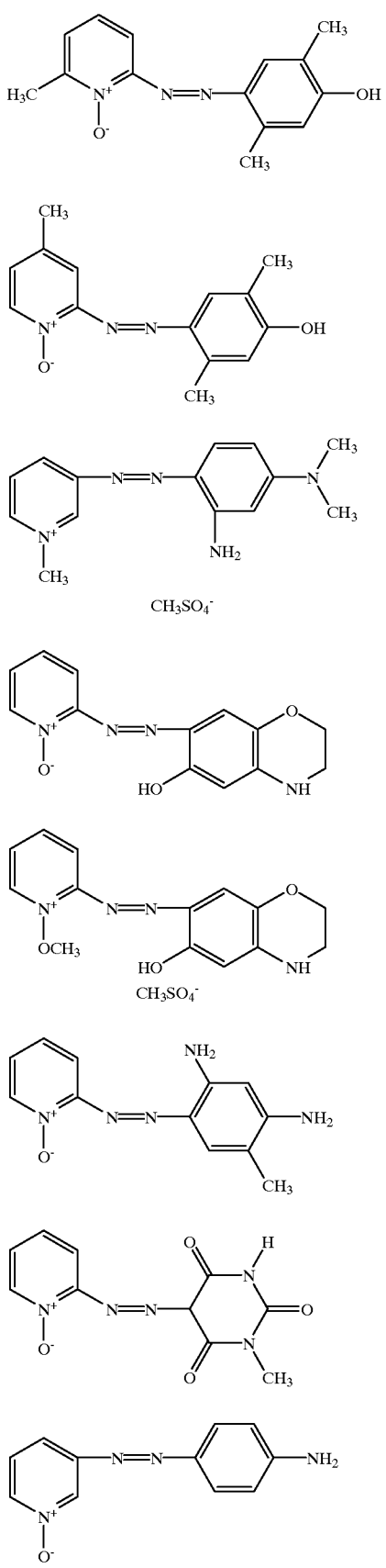

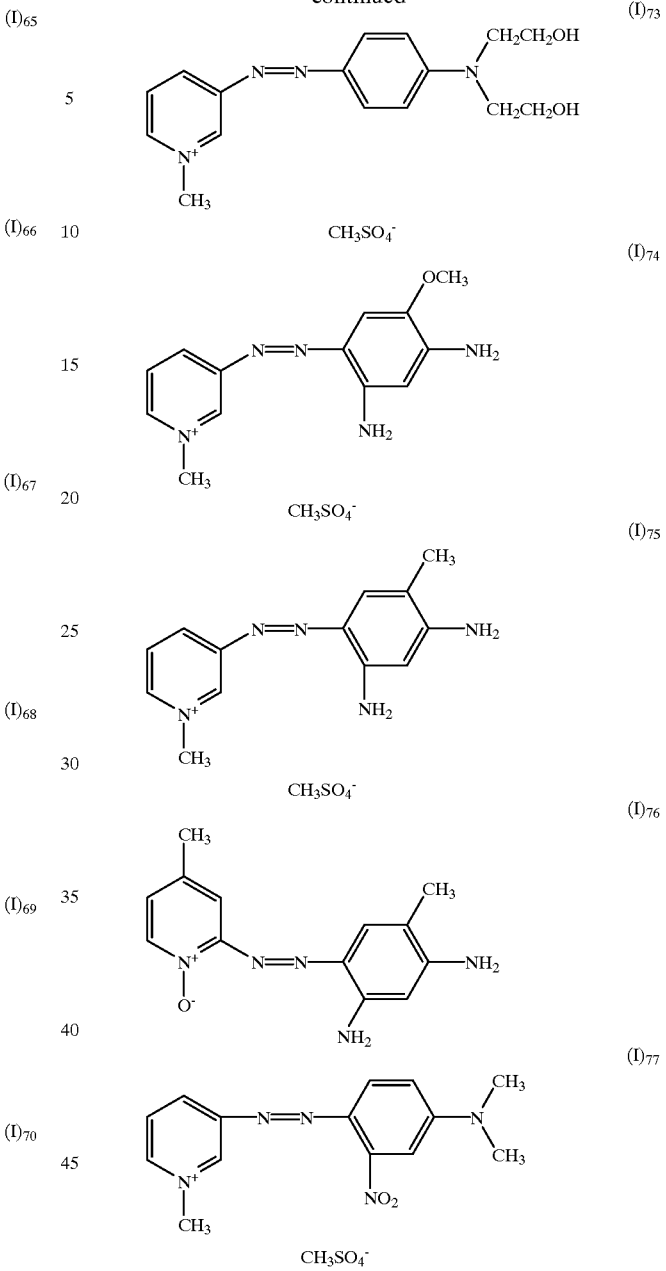

The cationic direct dye(s) used according to the invention preferably represent(s) from about 0.001 to about 10% by weight relative to the total weight of the dye composition, and even more preferably from about 0.005 to about 5% by weight relative to this weight.

(ii) The cationic or amphoteric substantive polymer which can be used according to the present invention is selected from:
  (1) dimethyldiallylammonium halide homopolymers and copolymers;
  (2) methacryloyloxyethyltrimethylammonium halide homopolymers and copolymers;
  (3) polyquaternary ammonium polymers chosen from those described below;
  (4) vinylpyrrolidone copolymers containing methacrylamidopropyltrimethylammonium or methylvinylimidazolium units; and
  (5) mixtures thereof.

The substantive nature, i.e., the ability to be deposited on the hair, of the polymers used according to the invention is determined conventionally using the test described by Richard J. Crawford, Journal of the Society of Cosmetic Chemists, 1980, 31-(5)-pages 273 to 278 (development by Red 80 acidic dye).

Among the substantive polymers of the methacryloyloxyethyltrimethylammonium halide homopolymer and copolymer type which can be used according to the invention, preferred polymers include the products referred to in the CTFA dictionary (5th edition, 1993) as "Polyquaternium 37", "Polyquaternium 32" and "Polyquaternium 35". "Polyquaternium 37" corresponds to the crosslinked poly(meth-acryloyloxyethyltrimethylammonium chloride) homopolymer, as a 50% dispersion in mineral oil, sold under the name Salcare SC95 by the company Allied Colloids. "Polyquaternium 32" corresponds to the crosslinked copolymer of acrylamide and of methacryloyloxyethyltrimethylammonium chloride (20/80 by weight), as a 50% dispersion in mineral oil, sold under the name Salcare SC92 by the company Allied Colloids. "Polyquaternium 35" corresponds to the methosulphate of the copolymer of methacryloyloxyethyltrimethylammonium and of methacryloyloxyethyidimethylacetylammonium, sold under the name Plex 7525L by the company Rohm GmbH.

Preferred substantive polymers of the dimethyldiallylammonium halide polymer type used according to the invention include:

dimethyldiallylammonium chloride homopolymers such as the one sold under the name "Merquat 100" by the company Merck;

copolymers of diallyldimethylammonium chloride and of acrylic acid, such as the one in proportions of 80/20 by weight sold under the name Merquat 280 by the company Calgon;

the copolymers of dimethyldiallylammonium chloride and of acrylamide sold under the names Merquat 550 and Merquat S by the company Merck.

Preferred substantive polymers of the polyquaternary ammonium type used according to the invention include:

the polymers prepared and described in French patent 2,270,846 (the disclosure of which is specifically incorporated by reference herein), comprising repeating units corresponding to formula (II) below:

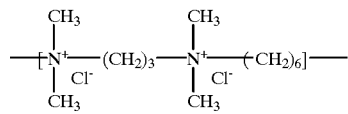

(II)

especially those in which the molecular weight, determined by gel permeation chromatography, ranges from 9500 to 9900;

the polymers prepared and described in French patent 2,270,846, comprising repeating units corresponding to formula (III) below:

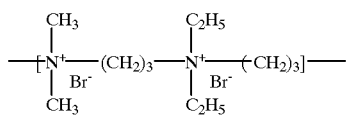

(III)

particularly those in which the molecular weight, determined by gel permeation chromatography, is about 1200;

the polymers described and prepared in U.S. Pat. Nos. 4,157,388, 4,390,689, 4,702,906 and 4,719,282 (the disclosures of which are specifically incorporated by reference herein) and comprising repeating units corresponding to formula (IV) below:

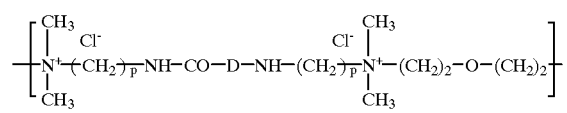

(IV)

in which p represents an integer ranging from 1 to 6 approximately, D can be absent or can represent a group —$(CH_2)_r$—CO— in which r represents a number equal to 4 or 7, the molecular mass of the said polymers preferably being less than 100,000, and more preferably less than or equal to 50,000; such polymers are sold in particular by the company Miranol under the names "Mirapol A15", "Mirapol AD1", "Mirapol AZ1" and "Mirapol 175".

Among the vinylpyrrolidone polymers (PVP) containing methacrylamidopropyltrimethylammonium (MAPTAC) units, preferred polymers include those sold under the trade names Gafquat ACP 1011 and Gafquat HS 100 by the company ISP.

Preferred vinylpyrrolidone polymers (PVP) containing methylvinylimidazolium units, include:

the PVP/methylvinylimidazolium chloride copolymers sold under the names Luviquat FC 370, FC 550, FC 905 and HM 552 by the company BASF, the PVP/methylvinylimidazolium chloride/vinylimidazole copolymer sold under the name Luviquat 8155 by the company BASF, the PVP/methylvinylimidazolium methosulphate copolymer sold under the name Luviquat MS 370 by the company BASF.

The concentration of substantive polymer (ii) in the dye composition according to the invention can preferably range from about 0.01 to about 10% relative to the total weight of the dye composition, and more preferably from about 0.1 to about 5%.

The medium suitable for dyeing (or support) generally comprises water or a mixture of water and at least one organic solvent to dissolve the compounds that would not be sufficiently water-soluble. Preferred organic solvents include $C_1$–$C_4$ lower alkanols such as ethanol and isopropanol; aromatic alcohols such as benzyl alcohol, as well as similar products and mixtures thereof.

The solvents can be present in proportions preferably ranging from about 1 to about 40% by weight relative to the total weight of the dye composition, and even more preferably from about 5 to about 30% by weight.

The pH of the dye composition in accordance with the invention generally ranges from about 2 to about 11, and preferably from about 5 to about 10. The pH can be adjusted to the desired value using acidifying or basifying agents usually used for dyeing keratin fibres.

Among the acidifying agents, examples include inorganic or organic acids such as hydrochloric acid, orthophosphoric acid, sulphuric acid, carboxylic acids such as acetic acid, tartaric acid, citric acid or lactic acid, and sulphonic acids.

Examples of basifying agents include aqueous ammonia, alkaline carbonates, alkanolamines such as mono-, di- and triethanolamine and derivatives thereof, sodium hydroxide, potassium hydroxide and the compounds of formula (V) below:

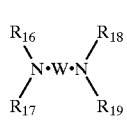

(V)

in which W is a propylene residue optionally substituted with a hydroxyl group or a $C_1$–$C_6$ alkyl radical; $R_{16}$, $R_{17}$, $R_{18}$ and $R_{19}$, which may be identical or different, represent a hydrogen atom or a $C_1$–$C_6$ alkyl or $C_1$–$C_6$ hydroxyalkyl radical.

In addition to the cationic direct dye(s) (i) defined above, the dye composition in accordance with the invention can contain one or more additional direct dyes which may be selected, for example, from nitrobenzene dyes, anthraquinone dyes, naphthoquinone dyes, triarylmethane dyes, xanthene dyes and azo dyes which are non-cationic.

When intended for oxidation dyeing, in addition to the cationic direct dye(s) (i), the dye composition in accordance with the invention comprises one or more oxidation bases selected from the oxidation bases conventionally used for oxidation dyeing, for example, para-phenylenediamines, bis(phenyl)alkylenediamines, para-aminophenols, ortho-aminophenols and heterocyclic bases.

When it is (they are) used, the oxidation base(s) preferably represent(s) an amount ranging from about 0.0005 to about 12% by weight relative to the total weight of the dye composition, and even more preferably from about 0.005 to about 6% by weight relative to this weight.

When intended for oxidation dyeing, in addition to the cationic direct dye (i) and the substantive polymer (ii) as well as oxidation bases, the dye composition in accordance with the invention can also contain at least one coupler so as to modify or enrich with glints the shades obtained using the cationic direct dye(s) (i) and the oxidation bases.

The couplers which can be used in the dye composition in accordance with the invention can be selected from the couplers used conventionally in oxidation dyeing, for example, meta-phenylenediamines, meta-aminophenols, meta-diphenols and heterocyclic couplers.

When it is present, the at least one coupler preferably represents an amount ranging from about 0.0001 to about 10% by weight relative to the total weight of the dye composition, and even more preferably from about 0.005 to about 5% by weight relative to this weight.

The dye composition in accordance with the invention can also contain various adjuvants conventionally used in compositions for dyeing the hair, such as antioxidants, penetrating agents, sequestering agents, fragrances, buffers, dispersing agents, surfactants, film-forming agents, ceramides, preserving agents, screening agents and opacifiers.

Needless to say, a person skilled in the art will take care to select this or these optional complementary compound(s) such that the advantageous properties intrinsically associated with the dye composition according to the invention are not, or are not substantially, adversely affected by the addition(s) envisaged.

The dye composition according to the invention can be in various forms, such as in the form of liquids, shampoos, creams or gels or any other form suitable for dyeing keratin fibres, particularly human hair. The dye composition can be obtained by mixing, at the time of use, a composition, which may be in pulverulent form, comprising the cationic dye(s) with a composition containing the specific substantive polymer(s).

When the combination of the cationic direct dye (i) and the substantive polymer (ii) according to the invention is used in a composition intended for oxidation dyeing, i.e., one or more oxidation bases are used, optionally in the presence of one or more couplers, or when it is used in a composition intended for lightening direct dyeing, then the dye composition in accordance with the invention further comprises at least one oxidizing agent selected, for example, from hydrogen peroxide, urea peroxide, alkali metal bromates, persalts such as perborates and persulphates, and enzymes such as peroxidases, laccases and two-electron oxidoreductases. The use of hydrogen peroxide or enzymes is particularly preferred.

Another subject of the invention is a process for dyeing keratin fibres, especially human keratin fibres such as the hair, using the dye composition as defined above.

According to a first variant of this dyeing process in accordance with the invention, at least one dye composition as defined above is applied to the fibres, for a period sufficient to develop the desired coloration, after which the fibres are rinsed, optionally washed with shampoo, rinsed again and dried.

The time required to develop the coloration on the keratin fibres generally ranges from 3 to 60 minutes and even more precisely from 5 to 40 minutes.

According to a second variant of this dyeing process in accordance with the invention, at least one dye composition as defined above is applied to the fibres, for a period sufficient to develop the desired coloration, without final rinsing.

According to one specific embodiment of this dyeing process, and when the dye composition in accordance with the invention contains at least one oxidation base and at least one oxidizing agent, the dyeing process includes a preliminary step which comprises separately storing, on the one hand, a composition (A1) comprising, in a medium suitable for dyeing, at least one cationic direct dye (i) as defined above and at least one oxidation base, and, on the other hand, a composition (B1) comprising, in a medium suitable for dyeing, at least one oxidizing agent, and then in mixing them together at the time of use, after which this mixture is applied to the keratin fibres, composition (A1) or composition (B1) containing the cationic or amphoteric substantive polymer (ii) as defined above.

According to another specific embodiment of this dyeing process, and when the dye composition in accordance with the invention contains at least one oxidizing agent, the dyeing process includes a preliminary step which comprises separately storing, on the one hand, a composition (A2) comprising, in a medium suitable for dyeing, at least one cationic direct dye (i) as defined above, and, on the other hand, a composition (B2) comprising, in a medium suitable for dyeing, at least one oxidizing agent, and then in mixing them together at the time of use, after which this mixture is applied to the keratin fibres, composition (A2) or composition (B2) containing the cationic or amphoteric substantive polymer as defined above.

Another subject of the invention is a multi-compartment dyeing device or "kit" or any other multi-compartment packaging system, a first compartment of which contains composition (A1) or (A2) as defined above and a second compartment of which contains composition (B1) or (B2) as defined above. These devices can be equipped with means for delivering the desired mixture onto the hair, such as the devices described in patent FR-2,586,913, the disclosure of which is specifically incorporated by reference herein, in the name of the L'Oréal.

The present invention is further illustrated by the following examples which are designed to teach those of ordinary skill in the art how to practice the invention. The following examples are intended to illustrate the invention without limiting its scope.

EXAMPLES

Example 1

The dye composition below was prepared:

| | | |
|---|---|---|
| Cationic direct dye of formula I(10) | | 0.12 g |
| Nonylphenol containing 9 mol of ethylene oxide | | 8.0 g |
| Substantive polymer of polyquaternary ammonium type of formula (II) | | 1.0 g A.M.* |
| Ethanol | | 10.0 g |
| 2-Amino-2-methyl-1-propanol | qs | pH 9 |
| Demineralized water | qs | 100.0 g |

A.M.*: Active material

The above composition was applied for 30 minutes to locks of natural grey hair containing 90% white hairs. The locks of hair were then rinsed, washed with a standard shampoo and then dried.

They were dyed in an intense red shade.

A similar result was obtained with the dye (I)1.

Example 2

The dye composition below was prepared:

| | | |
|---|---|---|
| Cationic direct dye of formula I(27) | | 0.10 g |
| Substantive polymer: diallyldimethyl-ammonium chloride homopolymer sold under the name Merquat 100 by the company Calgon | | 1.0 g A.M.* |
| Ethanol | | 10.0 g |
| Nonylphenol containing 9 mol of ethylene oxide | | 8.0 g |
| 2-Amino-2-methylpropanol | qs | pH 9 |
| Demineralized water | qs | 100 g |

A.M.*: Active material

The above composition was applied for 30 minutes to locks of natural grey hair containing 90% white hairs. The locks of hair were then rinsed, washed with a standard shampoo and then dried.

They were dyed in an intense purple shade.

A similar result was obtained with the dye (I)32.

The foregoing written description relates to various embodiments of the present invention. Numerous changes and modifications may be made therein without departing from the spirit and scope of the invention as defined in the following claims.

What is claimed is:

1. A composition for dyeing keratin fibers comprising:

(i) at least one cationic direct dye chosen from cationic direct dyes of structures $(I)_1$ to $(I)_{77}$ below:

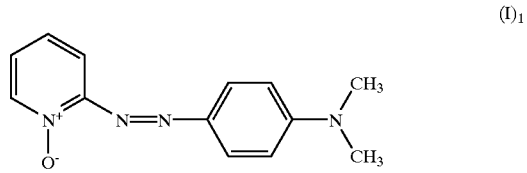

$(I)_1$

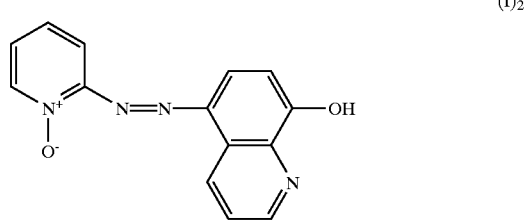

$(I)_2$

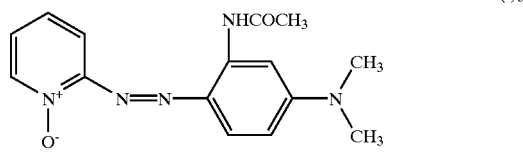

$(I)_3$

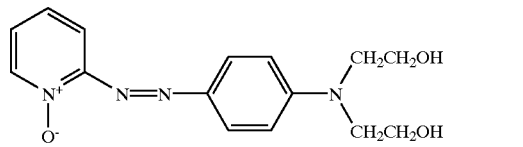

$(I)_4$

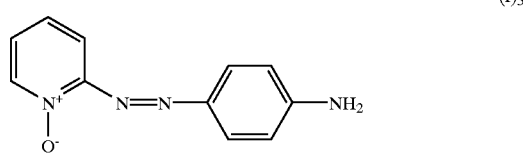

$(I)_5$

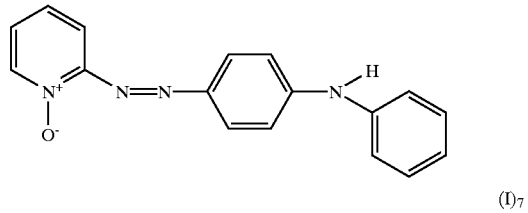

$(I)_6$

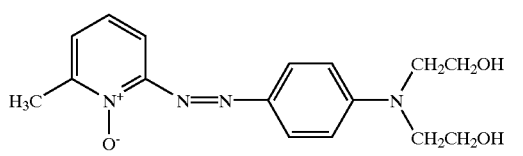

$(I)_7$

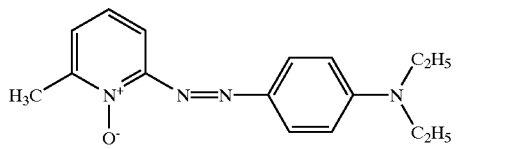

$(I)_8$

-continued
(I)9
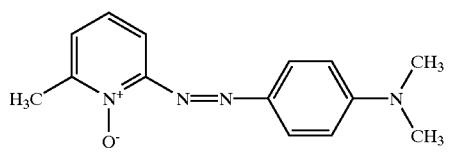
(I)10
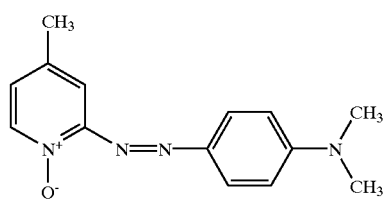
(I)11
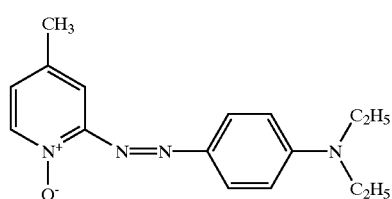
(I)12
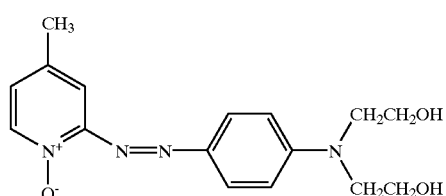
(I)13
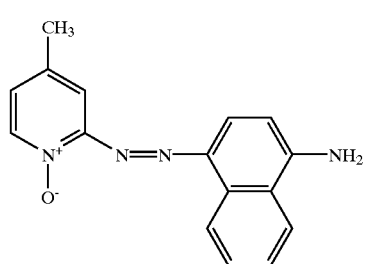
(I)14
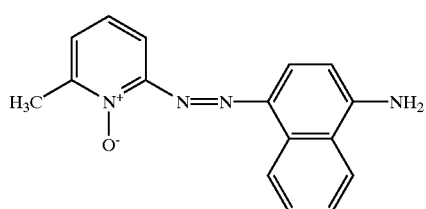
(I)15
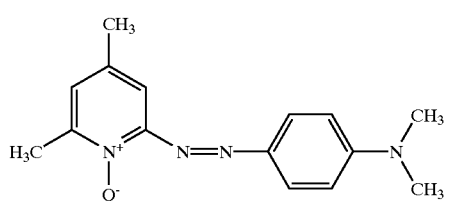
(I)16
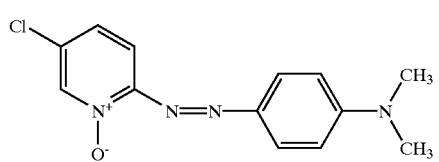
-continued
(I)17
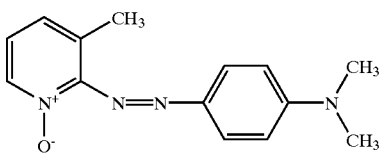
(I)18
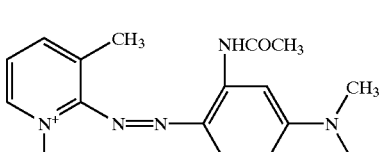
(I)19
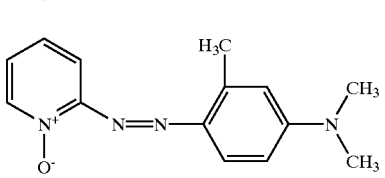
(I)20
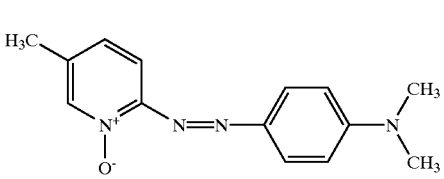
(I)21
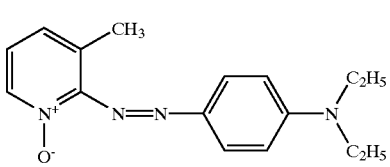
(I)22
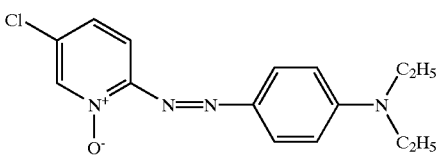
(I)23
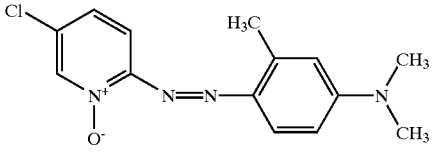
(I)24
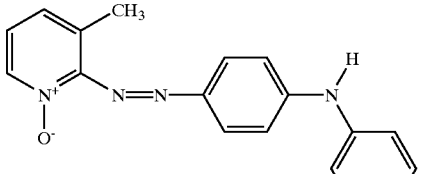
(I)25
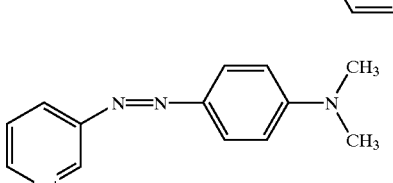

-continued
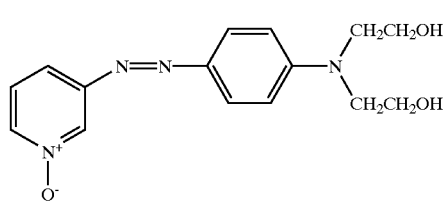
(I)26
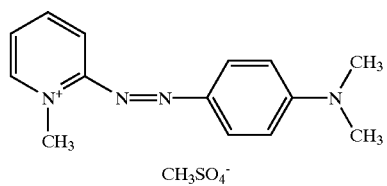
(I)27
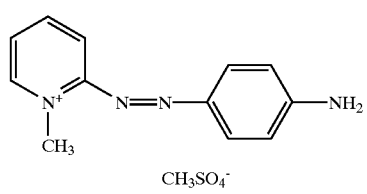
(I)28
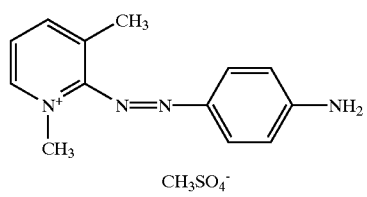
(I)29
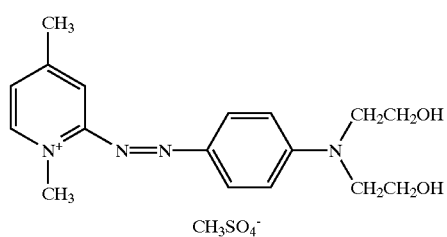
(I)30
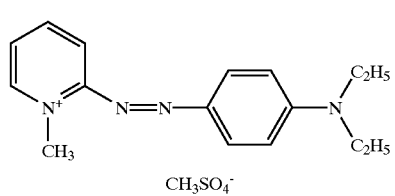
(I)31
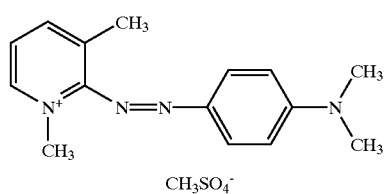
(I)32
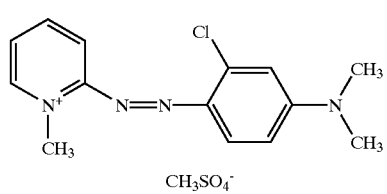
(I)33
-continued
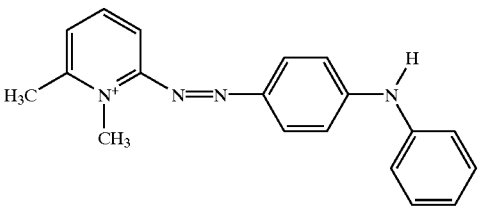
(I)34
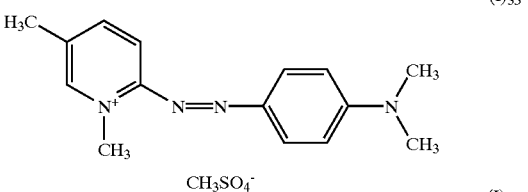
(I)35
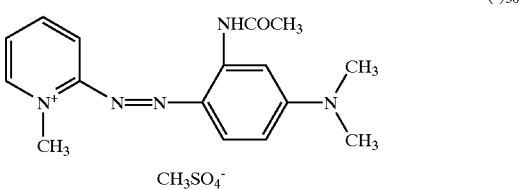
(I)36
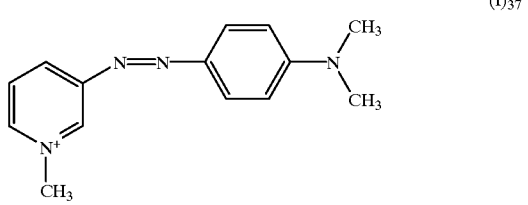
(I)37
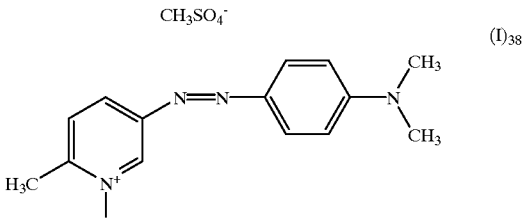
(I)38
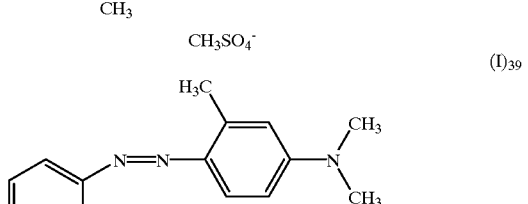
(I)39
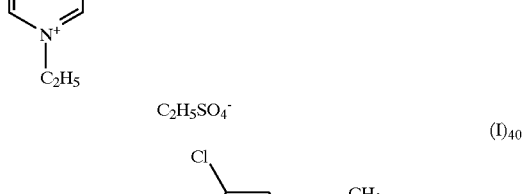
(I)40
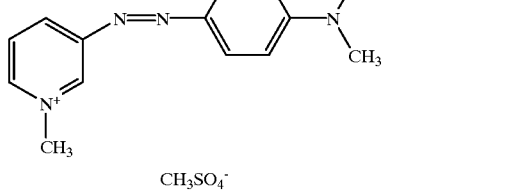

-continued (I)₄₁ — pyridinium-azo-phenyl-NH-phenyl; CH₃SO₄⁻

(I)₄₂ — pyridinium(C₂H₅)-azo-[2-NHCOCH₃, 4-N(CH₃)₂]phenyl; C₂H₅SO₄⁻

(I)₄₃ — pyridinium(C₄H₉)-azo-[2-CH₃, 4-N(CH₃)₂]phenyl; Br⁻

(I)₄₄ — pyridinium(OCH₃)-azo-pyrazolone (3-CH₃, 1-C₆H₅); CH₃SO₄⁻

(I)₄₅ — pyridinium N-oxide-azo-barbituric acid (I)₄₆ — benzothiazolium(CH₃)-azo-[4-N(CH₃)₂]phenyl; ClO₄⁻

(I)₄₇ — benzimidazolium(1,3-diCH₃)-azo-[4-N(CH₃)₂]phenyl; ClO₄⁻

(I)₄₈ — pyridinium N-oxide-azo-[2,6-diamino]pyridine (I)₄₉ — benzothiazolium(CH₃)-azo-[5-CH₃, 2,4-diNH₂]phenyl; I⁻

(I)₅₀ — thiazolium(4-CH₃, 3-C₆H₅)-azo-benzoxazine-OH; ClO₄⁻

(I)₅₁ — benzothiazolium(CH₃)-azo-benzoxazine-OH; Cl⁻

(I)₅₂ — thiazolium(4,3-diC₆H₅)-azo-benzoxazine-OH; ClO₄⁻

(I)₅₃ — pyridinium N-oxide-azo-[2,4-diNH₂, 5-OCH₃]phenyl (I)₅₄ — pyridinium N-oxide-azo-[2-CH₃, 4-OH, 5-NHCOCH₃]phenyl

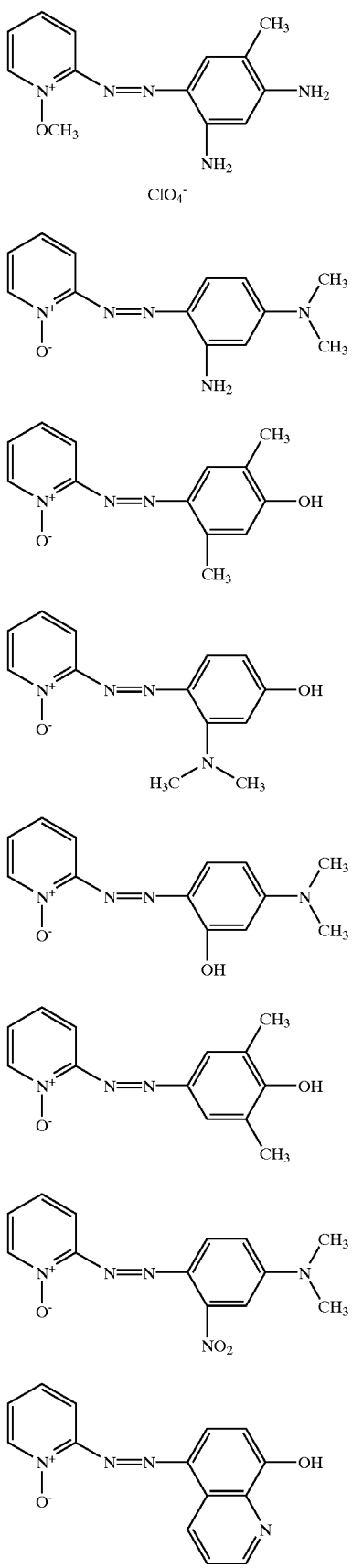
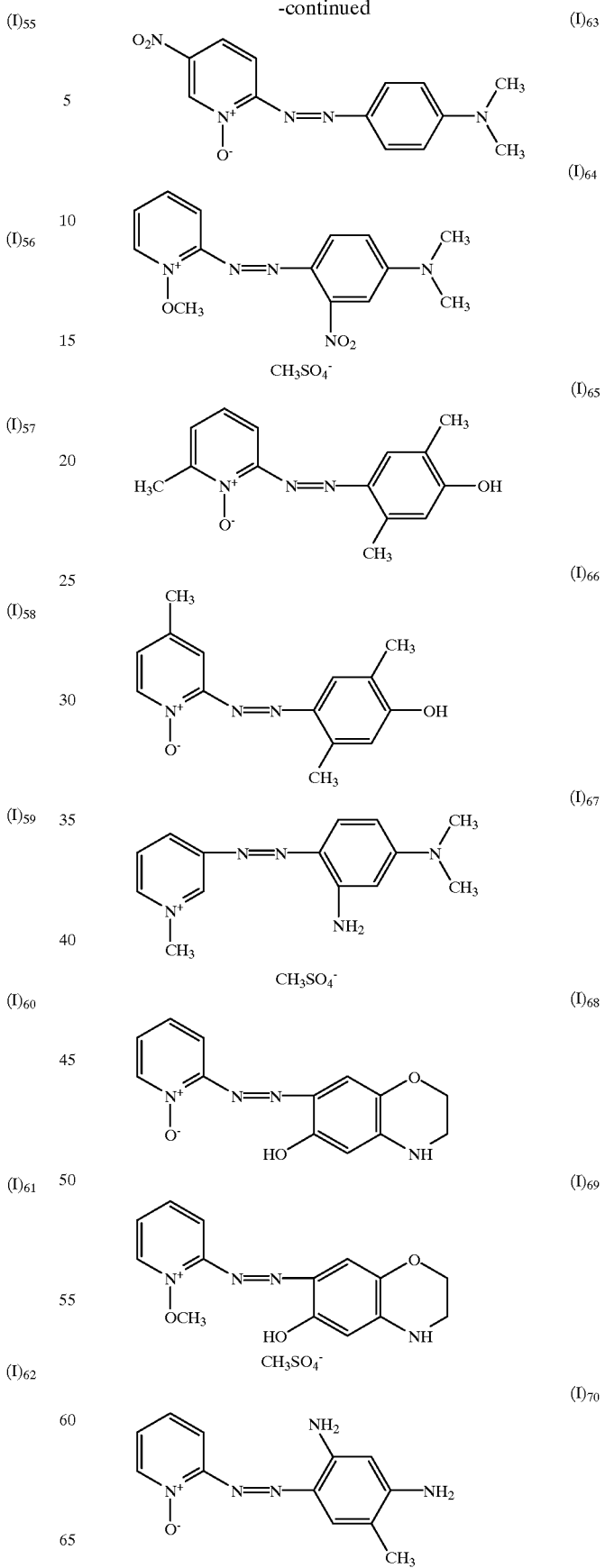

-continued (I)₇₁ — 2-(1-oxidopyridinium-2-yl)azo-1-methylbarbituric acid derivative structure (I)₇₂ — 3-[(4-aminophenyl)azo]-1-methylpyridinium 1-oxide; CH₃SO₄⁻

(I)₇₃ — 3-[[4-[bis(2-hydroxyethyl)amino]phenyl]azo]-1-methylpyridinium; CH₃SO₄⁻

(I)₇₄ — 3-[[2,4-diamino-5-methoxyphenyl]azo]-1-methylpyridinium; CH₃SO₄⁻

(I)₇₅ — 3-[(2,4-diamino-5-methylphenyl)azo]-1-methylpyridinium; CH₃SO₄⁻

(I)₇₆ — 2-[(2,4-diamino-5-methylphenyl)azo]-4-methylpyridinium 1-oxide (I)₇₇ — 3-[[4-(dimethylamino)-2-nitrophenyl]azo]-1-methylpyridinium; CH₃SO₄⁻ and (ii) at least one polymer chosen from cationic and amphoteric substantive polymers chosen from:
(1) dimethyldiallylammonium halide homopolymers and copolymers;
(2) methacryloyloxyethyltrimethylammonium halide homopolymers and copolymers
(3) polyquaternary ammonium polymers chosen from:
polymers comprising repeating units corresponding to formula (II) below:

$$-\left[N^+(CH_3)_2-(CH_2)_3-N^+(CH_3)_2-(CH_2)_6\right]- \quad 2Cl^- \tag{II}$$

polymers comprising repeating units corresponding to formula (III) below:

$$-\left[N^+(CH_3)_2-(CH_2)_3-N^+(C_2H_5)_2-(CH_2)_3\right]- \quad 2Br^- \tag{III}$$

polymers comprising repeating units corresponding to formula (IV) below:

$$-\left[N^+(CH_3)_2-(CH_2)_p-NH-CO-D-NH-(CH_2)_p-N^+(CH_3)_2-(CH_2)_2-O-(CH_2)_2\right]- \quad 2Cl^- \tag{IV}$$

wherein p is chosen from integers ranging from about 1 to about 6,
D is absent or is a —(CH₂)ᵣCO— group, wherein r represents a number equal to 4 or 7; and
(4) vinylpyrrolidone copolymers comprising units chosen from methacrylamidopropyltrimethylammonium units and methylvinylimidazolium units.

2. A composition according to claim 1, wherein said keratin fibers are human keratin fibers.

3. A composition according to claim 2, wherein said human keratin fibers are human hair.

4. A composition according to claim 1, wherein said composition is in a medium suitable for dyeing.

5. A composition according to claim 1, wherein said at least one cationic direct dye is present in an amount ranging from about 0.001 to about 10% by weight relative to the total weight of the composition.

6. A composition according to claim 5, wherein said at least one cationic direct dye is present in an amount ranging from about 0.005 to about 5% by weight relative to the total weight of the composition.

7. A composition according to claim 1, wherein said cationic and amphoteric substantive polymers are chosen from dimethyldiallylammonium chloride homopolymer.

8. A composition according to claim 1, wherein said cationic and amphoteric substantive polymers are chosen from a copolymer of dimethyldiallylammonium chloride and of acrylic acid (80/20 by weight).

9. A composition according to claim 1, wherein said cationic and amphoteric substantive polymers are chosen from crosslinked methacryloyloxyethyltrimethylammonium chloride homopolymers, as a 50% dispersion in mineral oil, crosslinked copolymers of acrylamide and of methacryloyloxyethyltrimethylammonium chloride (20/80 by weight), as a 50% dispersion in mineral oil, and a methosulphate of the copolymers of methacryloyloxyethyltrimethylammonium and of methacryloyloxyethyldimethylacetylammonium.

10. A composition according to claim 1, wherein said at least one polymer represents an amount ranging from about 0.01 to about 10% by weight relative to the total weight of the composition.

11. A composition according to claim 10, wherein said at least one polymer represents an amount ranging from 0.1 to 5% by weight relative to the total weight of the composition.

12. A composition according to claim 4, wherein said at least one medium suitable for dyeing comprises water or a mixture of water and at least one organic solvent.

13. A composition according to claim 1, having a pH ranging from out 2 to about 11.

14. A composition according to claim 13, having a pH ranging from about 5 to about 10.

15. A composition according to claim 1, further comprising at least one oxidation base.

16. A composition according to claim 15, wherein said at least one oxidation base is chosen from para-phenylenediamines, bis(phenyl)alkylenediamines, para-aminophenols, ortho-aminophenols and heterocyclic bases.

17. A composition according to claim 15, wherein said at least one oxidation base represents an amount ranging from about 0.0005 to about 12% by weight relative to the total weight of the dye composition.

18. A composition according to claim 17, wherein said at least one oxidation base represents an amount ranging from about 0.005 to about 6% by weight relative to the total weight of the dye composition.

19. A composition according to claim 15, further comprising at least one coupler.

20. A composition according to claim 19, wherein said at least one coupler is chosen from meta-phenylenediamines, meta-aminophenols, meta-diphenols and heterocyclic couplers.

21. A composition according to claim 19, wherein said at least one coupler represents an amount ranging from about 0.0001 to about 10% by weight relative to the total weight of the dye composition.

22. A composition according to claim 21, wherein said at least one coupler represents an amount ranging from about 0.005 to about 5% by weight relative to the total weight of the dye composition.

23. A composition according to claim 1, further comprising at least one oxidizing agent.

24. A composition according to claim 23, wherein said at least one oxidizing agent is chosen from hydrogen peroxide, urea peroxide, alkali metal bromate, a persalt, and an enzyme.

25. A method for dyeing keratin fibers, said method comprising applying to said keratin fibers at least one dyeing composition comprising:
(i) at least one cationic direct dye chosen from cationic direct dyes of structures $(I)_1$ to $(I)_{77}$ below:

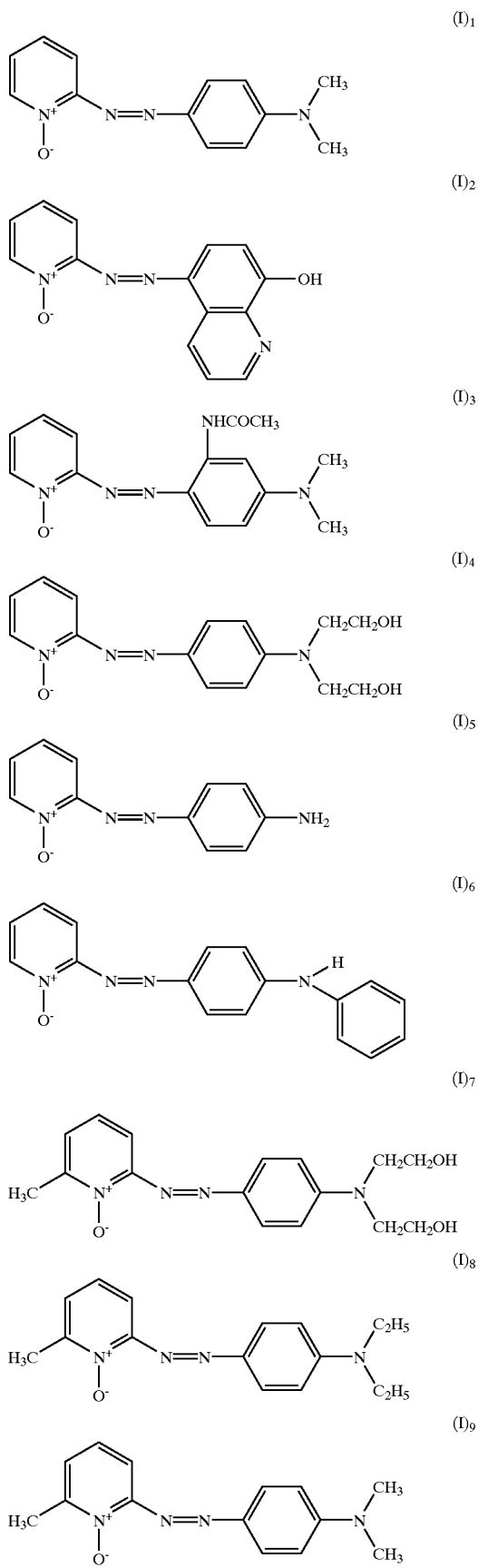

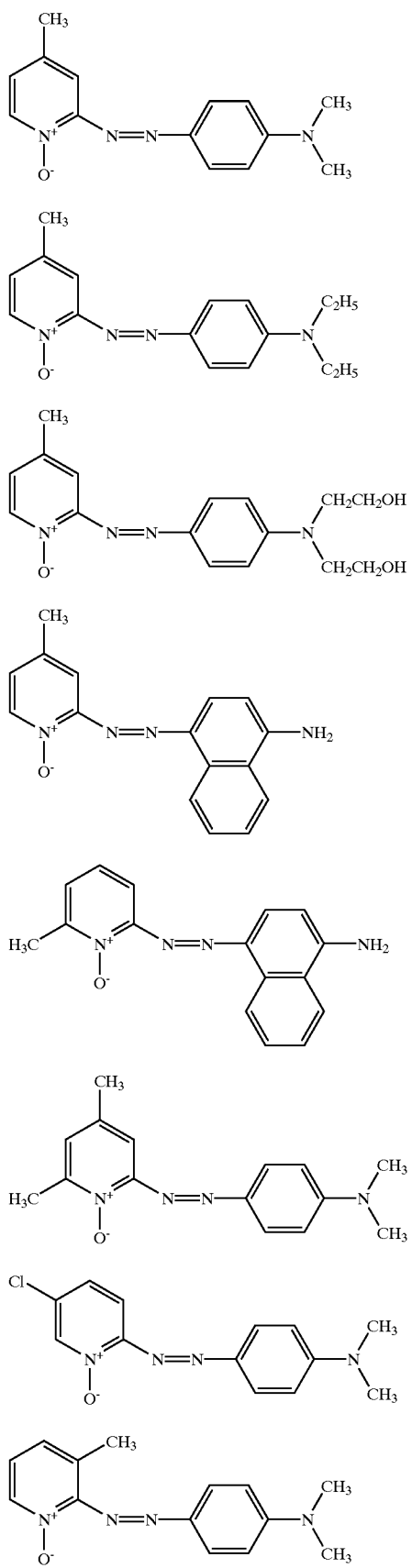
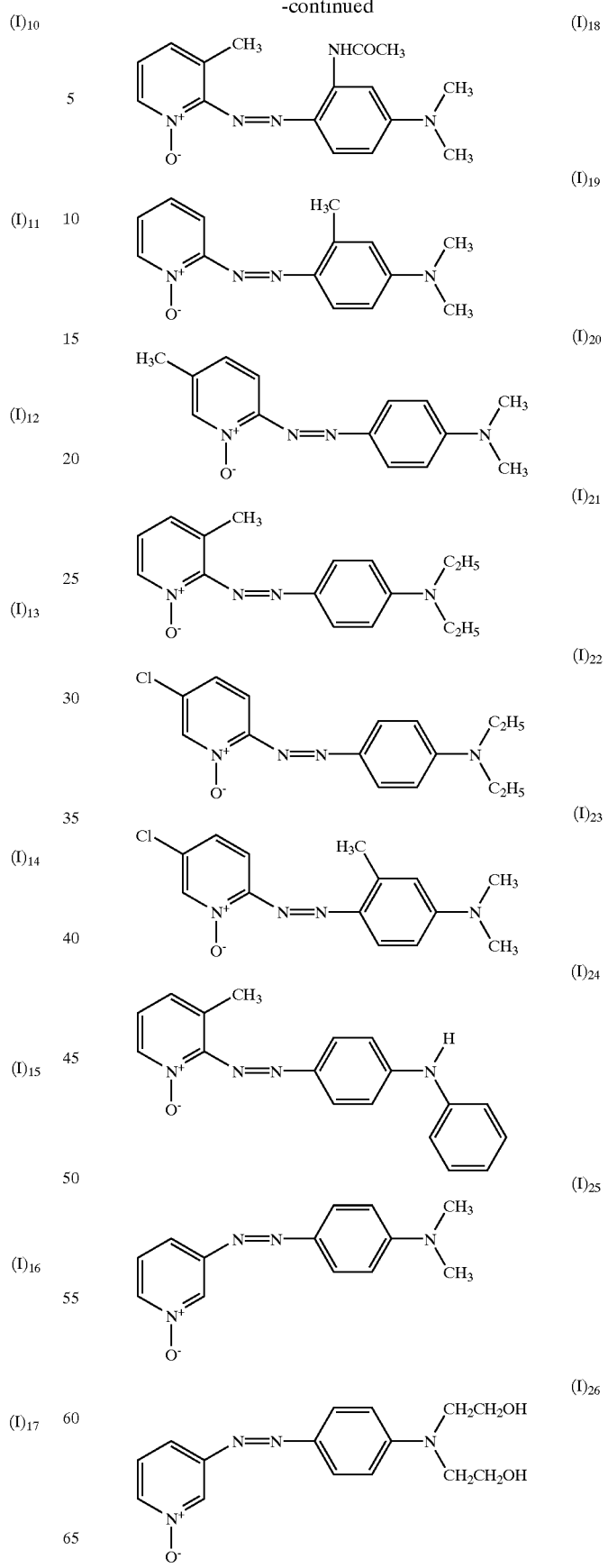

-continued
(I)27
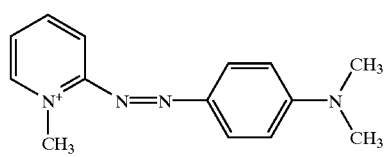
(I)28
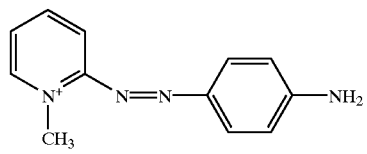
(I)29
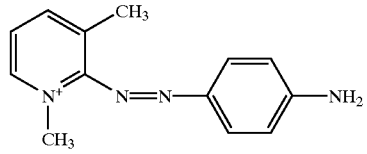
(I)30
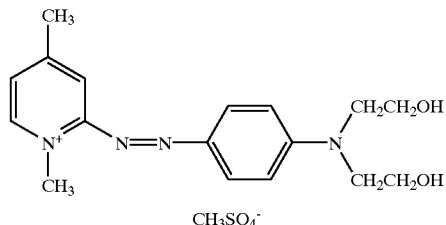
(I)31
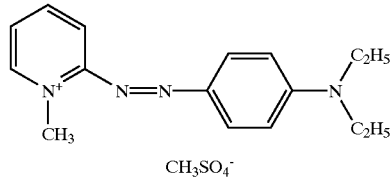
(I)32
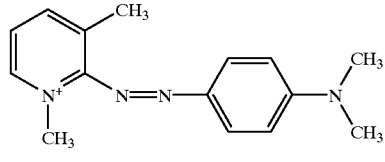
(I)33
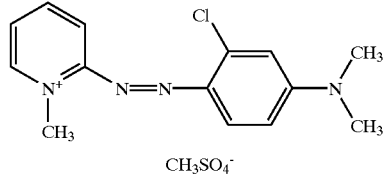
(I)34
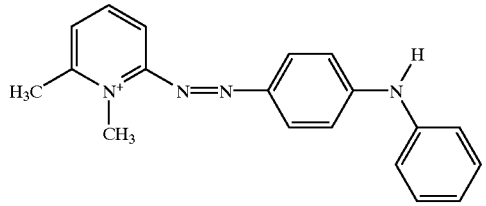
-continued
(I)35
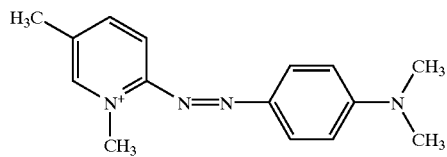
(I)36
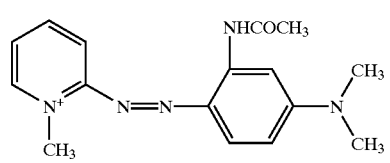
(I)37
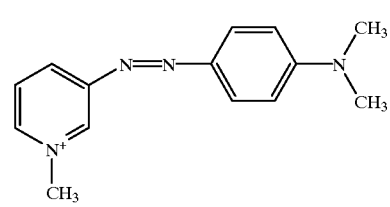
(I)38
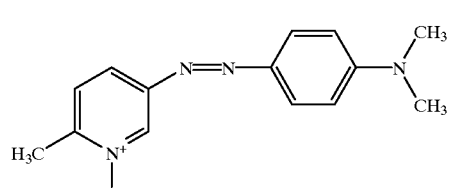
(I)39
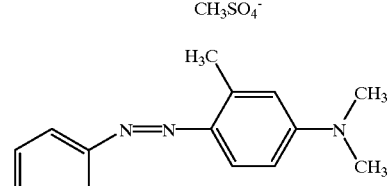
(I)40
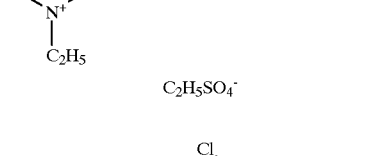
(I)41
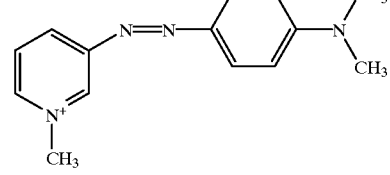

-continued (I)₄₂ — pyridinium azo dimethylaminophenyl with NHCOCH₃ substituent; N⁺-C₂H₅; C₂H₅SO₄⁻

(I)₄₃ — pyridinium azo dimethylaminotolyl; N⁺-C₄H₉; Br⁻

(I)₄₄ — pyridinium azo pyrazolone (3-methyl-1-phenyl-5-oxo); N⁺-OCH₃; CH₃SO₄⁻

(I)₄₅ — pyridinium N-oxide azo barbituric acid (I)₄₆ — benzothiazolium (N-CH₃) azo 4-(dimethylamino)phenyl; ClO₄⁻

(I)₄₇ — 1,3-dimethylbenzimidazolium azo 4-(dimethylamino)phenyl; ClO₄⁻

(I)₄₈ — pyridinium N-oxide azo 2,6-diaminopyridine (I)₄₉ — benzothiazolium (N-CH₃) azo (2,4-diamino-5-methylphenyl); I⁻

(I)₅₀ — 4-methyl-3-phenylthiazolium azo (6-hydroxy-3,4-dihydro-2H-1,4-benzoxazin-7-yl); ClO₄⁻

(I)₅₁ — benzothiazolium (N-CH₃) azo (6-hydroxy-3,4-dihydro-2H-1,4-benzoxazin-7-yl); Cl⁻

(I)₅₂ — 3,4-diphenylthiazolium azo (6-hydroxy-3,4-dihydro-2H-1,4-benzoxazin-7-yl); ClO₄⁻

(I)₅₃ — pyridinium N-oxide azo (2,4-diamino-5-methoxyphenyl)

(I)₅₄ — pyridinium N-oxide azo (4-hydroxy-2-methyl-5-acetamidophenyl)

(I)₅₅ — pyridinium (N-OCH₃) azo (2,4-diamino-5-methylphenyl); ClO₄⁻

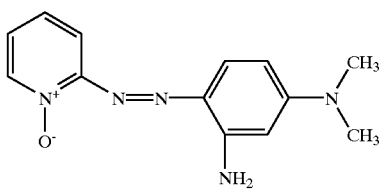 (I)56
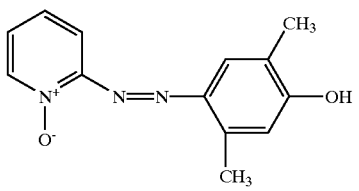 (I)57
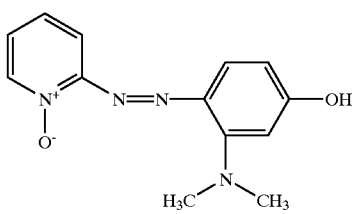 (I)58
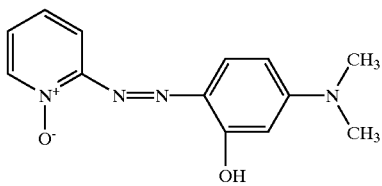 (I)59
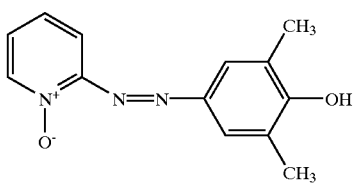 (I)60
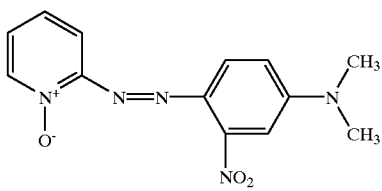 (I)61
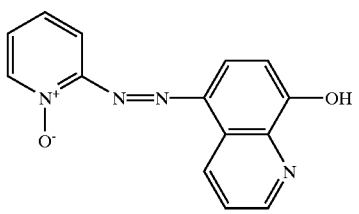 (I)62
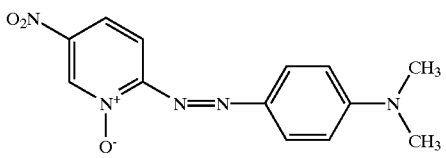 (I)63
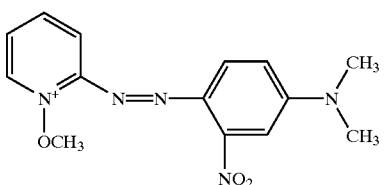 (I)64
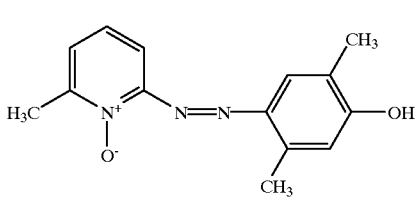 (I)65
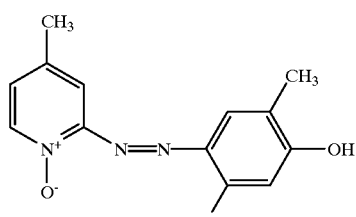 (I)66
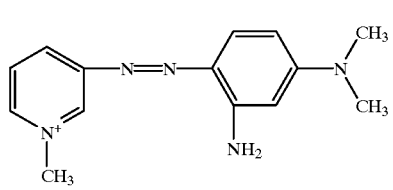 (I)67
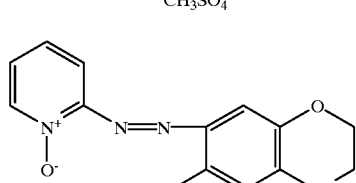 (I)68
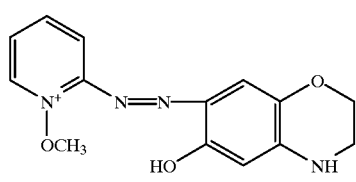 (I)69
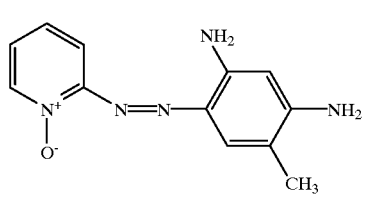 (I)70
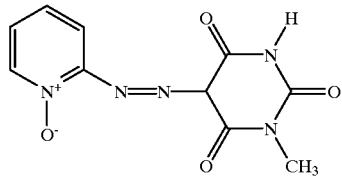 (I)71

-continued

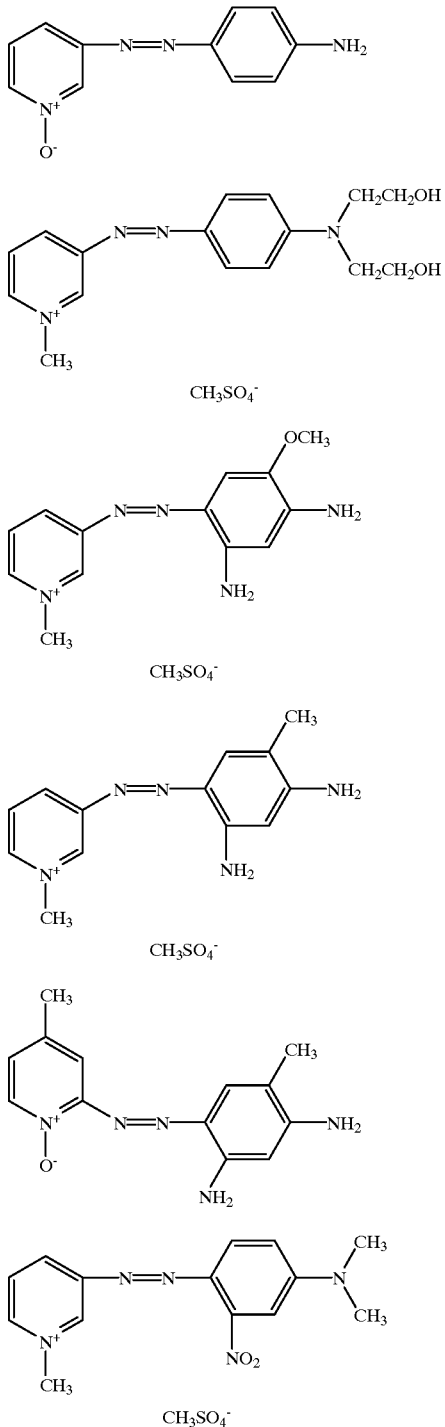

and
(ii) at least one polymer chosen from cationic and amphoteric substantive polymers chosen from:
(1) dimethyldiallylammonium halide homopolymers and copolymers;
(2) methacryloyloxyethyltrimethylammonium halide homopolymers and copolymers
(3) polyquaternary ammonium polymers chosen from: polymers comprising repeating units corresponding to formula (II) below:

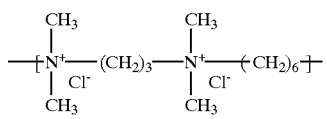

polymers comprising repeating units corresponding to formula (III) below:

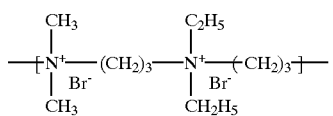

polymers comprising repeating units corresponding to formula (IV) below:

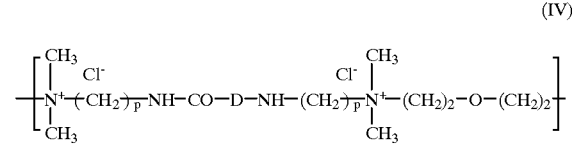

wherein p is chosen from integers ranging from about 1 to about 6,

D is absent or is a —$(CH_2)_r$—CO— group, wherein r represents a number equal to 4 or 7; and (4) vinylpyrrolidone copolymers comprising units chosen from methacrylamidopropyltrimethylammonium units and methylvinylimidazolium units, and allowing said at least one dyeing composition to remain on said keratin fibers for a period of time sufficient to develop the desired coloration.

26. A method for dyeing keratin fibers according to claim 25, further comprising rinsing said keratin fibers after said period of time sufficient to develop the desired coloration.

27. A method for dyeing keratin fibers according to claim 26, further comprising, after said rinsing, washing said keratin fibers with shampoo, rinsing said keratin fibers again, and drying said keratin fibers.

28. The method according to claim 26, wherein said period of time ranges from 3 to 60 minutes.

29. The method according to claim 28, wherein said period of time ranges from 5 to 40 minutes.

30. A method for dyeing keratin fibers, said method comprising (i) mixing a first composition with a second composition, said first composition comprising, in a medium suitable for dyeing, at least one cationic direct dye of formula (I) below:

wherein:
the symbol A is chosen from structures A1 to A3 below:

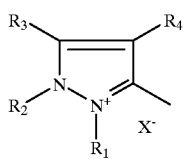
A1

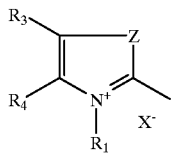
A2

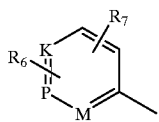
A3 wherein in structures A1 to A3,
$R_1$ is chosen from $C_1$–$C_4$ alkyl radicals and phenyl radicals which are unsubstituted or have a substituent chosen from $C_1$–$C_4$ alkyl radicals and halogen atoms chosen from chlorine, bromine, iodine and fluorine;
$R_2$ is chosen from $C_1$–$C_4$ alkyl radicals and phenyl radicals;
$R_3$ and $R_4$ are identical or different and are chosen from $C_1$–$C_4$ alkyl radicals and phenyl radicals, and
wherein when said A is said structure A1, can together form a substituted benzene ring, or
wherein when said A is said structure A2, can together form a benzene ring optionally substituted with at least one radical chosen from $C_1$–$C_4$ alkyl radicals, $C_1$–$C_4$ alkoxy radicals and $NO_2$ radicals;
$R_3$ can also represent a hydrogen atom;
Z is chosen from an oxygen atom, a sulphur atom and —$NR_2$ groups;
M is chosen from a —OH group, —OR groups, wherein R is chosen from $C_1$–$C_4$ alkyl radicals, and $N^+R_5(X^-)_r$ groups, wherein r is 0 or 1;
K is chosen from a —CH group, —CR groups wherein R is chosen from $C_1$–$C_4$ alkyl radicals and —$N^-R_5(X^-)_r$ groups, wherein r is 0 or 1;
P is chosen from a —CH group, —CR groups, wherein R is chosen from $C_1$–$C_4$ alkyl radicals and —$N^+R_5(X^-)_r$ groups, wherein r is 0 or 1;
$R_5$ is chosen from an $O^-$, $C_1$–$C_4$ alkoxy radicals and $C_1$–$C_4$ alkyl radicals;
$R_6$ and $R_7$, are identical or different and are chosen from a hydrogen atom, a halogen atom chosen from chlorine, bromine, iodine and fluorine, $C_1$–$C_4$ alkyl radicals, $C_1$–$C_4$ alkoxy radicals and —$NO_2$ radicals;
$X^-$ represents an anion;
with the provisos that,
if $R_4$ is a $C_1$–$C_4$ alkyl radical and Z is a sulphur atom, then $R_3$ is not a hydrogen atom
if $R_5$ is $O^-$, then r is zero;
if K or P or M are —$N^+$—$C_1$–$C_4$-alkyl $X^-$, then $R_6$ or $R_7$ is not a hydrogen atom, excepting said cationic direct dyes of formulae $(I_{27})$,$(I_{28})$,$(I_{31})$,$(I_{33})$,$(I_{36})$,$(I_{37})$,$(I_{39})$-$(I_{43})$,$(I_{67})$,$(I_{73})$-$(I_{75})$, and $(I_{77})$ below:

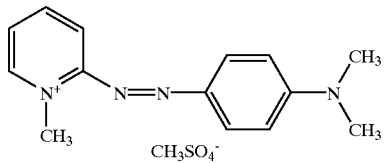
$(I)_{27}$

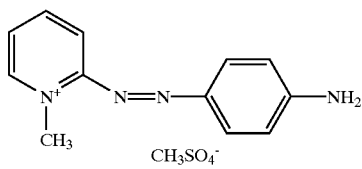
$(I)_{28}$

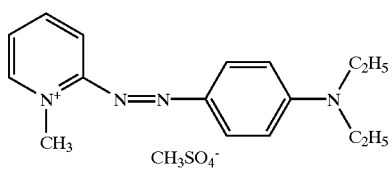
$(I)_{31}$

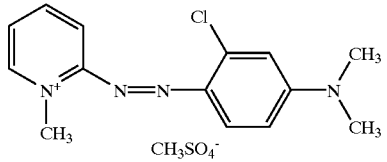
$(I)_{33}$

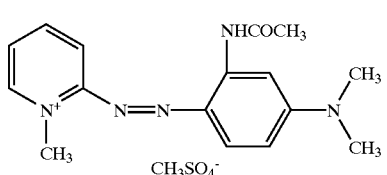
$(I)_{36}$

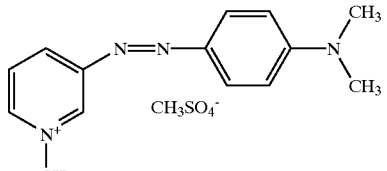
$(I)_{37}$

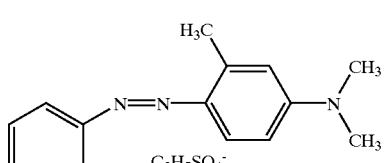
$(I)_{39}$

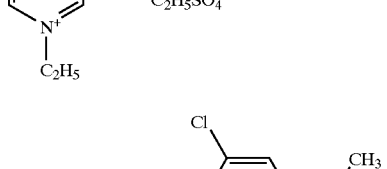
$(I)_{40}$

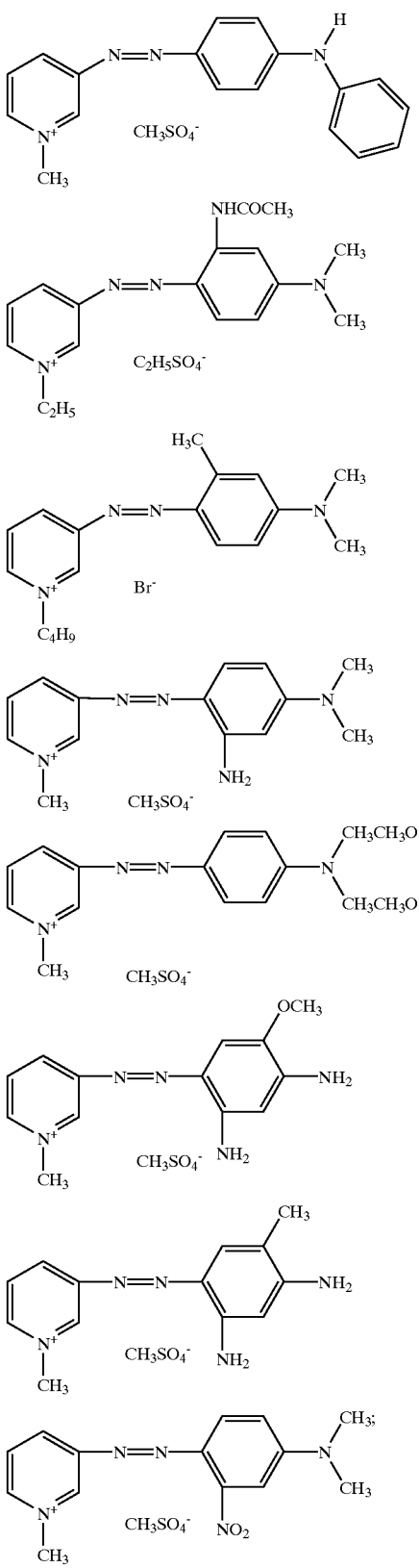

if K is —N⁺R₅(X⁻)ᵣ, then M=P=—CH or —CR;
if M is —N⁺R₅(X⁻)ᵣ, then K=P=—CH or —CR;
if P is —N⁺R₅(X⁻)ᵣ, then K=M=—CH or —CR wherein at least one of K, M, or P is —N⁺R₅(X⁻)ᵣ;
if Z is —NR₂ and R₂ is a C₁–C₄ alkyl radical, then at least one of said radicals R₁, R₃ or R₄ on A₂ is not a C₁–C₄ alkyl radical;

the symbol B represents:
(a) a group of structure B1 below:

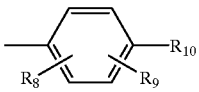

wherein in said structure B1,

R₈ is chosen from a hydrogen atom, a halogen atom chosen from chlorine, bromine, iodine and fluorine, C₁–C₄ alkyl radicals, C₁–C₄ alkoxy radicals, an —OH radical, an —NO₂, —NHR₁₁ radicals, —NR₁₂R₁₃ radicals and —NHCO(C₁–C₄)alkyl radicals or forms, with R₉, a 5- or 6-membered ring which may or may not contain one or more hetero atoms chosen from nitrogen, oxygen and sulphur;

R₉ is chosen from a hydrogen atom, a halogen atom chosen from chlorine, bromine, iodine and fluorine, C₁–C₄ alkyl radicals, and C₁–C₄ alkoxy radicals, or forms, with R₁₀ or R₁₁, a 5- or 6-membered ring which may or may not contain at least one hetero atom chosen from nitrogen, oxygen and sulphur;

R₁₀ is chosen from a hydrogen atom, an —OH radical, —NHR₁₁ radicals and —NR₁₂R₁₃ radicals;

R₁₁ is chosen from a hydrogen atom, C₁–C₄ alkyl radicals, C₁–C₄ monohydroxyalkyl radicals, C₂–C₄ polyhydroxyalkyl radicals and a phenyl radical;

R₁₂ and R₁₃, are identical or different and are chosen from C₁–C₄ alkyl radicals, C₁–C₄ monohydroxyalkyl radicals and C₂–C₄ polyhydroxyalkyl radicals; or (b) a 5- or 6-membered nitrogenous heterocyclic group which can contain other hetero atoms and/or carbonyl groups and which is unsubstituted or substituted with at least one radical chosen from C₁–C₄ alkyl radicals, amino radicals, and phenyl radicals, and at least one oxidation base, said second composition comprising, in a medium suitable for dyeing, at least one oxidizing agent, wherein said first composition or said second composition contain at least one polymer chosen from cationic and amphoteric substantive polymers chosen from:

(1) dimethyldiallylammonium halide homopolymers and copolymers;
(2) methacryloyloxyethyltrimethylammonium halide homopolymers and copolymers
(3) polyquaternary ammonium polymers chosen from: polymers comprising repeating units corresponding to formula (II) below:

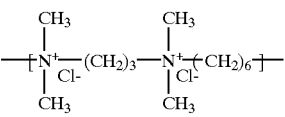

polymers comprising repeating units corresponding to formula (III) below:

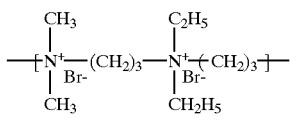
(III)

polymers comprising repeating units corresponding to formula (IV) below:

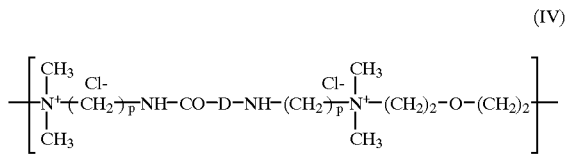
(IV)

wherein p is chosen from integers ranging from about 1 to about 6,

D is absent or is a —(CH$_2$)$_r$—CO— group, wherein r represents a number equal to 4 or 7; and (4) vinylpyrrolidone copolymers comprising units chosen from methacrylamidopropyltrimethylammonium units and methylvinylimidazolium units, and (ii) applying said mixture of said first composition and said second composition to said keratin fibers for a period of time sufficient to dye said keratin fibers, wherein said mixing occurs before the time of application of said first and second compositions to said keratin fibers.

31. A method for dyeing keratin fibers, said method comprising (i) mixing a first composition with a second composition, said first composition comprising, in a medium suitable for dyeing, at least one cationic direct dye of formula (I) below:

A—N=N—B (I)

wherein:

the symbol A is chosen from structures A1 to A3 below:

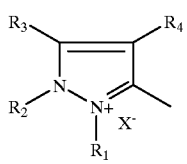
A1

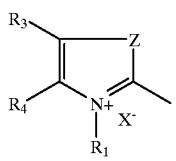
A2

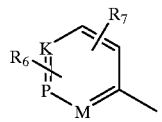
A3 wherein in structures A1 to A3, $R_1$ is chosen from $C_1$–$C_4$ alkyl radicals and phenyl radicals which are unsubstituted or have a substituent chosen from $C_1$–$C_4$ alkyl radicals and halogen atoms chosen from chlorine, bromine, iodine and fluorine;

$R_2$ is chosen from $C_1$–$C_4$ alkyl radicals and phenyl radicals;

$R_3$ and $R_4$ are identical or different and are chosen from $C_1$–$C_4$ alkyl radicals and phenyl radicals, and
wherein when said A is said structure A1, can together form a substituted benzene ring, or
wherein when said A is said structure A2, can together form a benzene ring optionally substituted with at least one radical chosen from $C_1$–$C_4$ alkyl radicals, $C_1$–$C_4$ alkoxy radicals and NO$_2$ radicals;

$R_3$ can also represent a hydrogen atom;

Z is chosen from an oxygen atom, a sulphur atom and —NR$_2$ groups;

M is chosen from a —OH group, —OR groups, wherein R is chosen from $C_1$–$C_4$ alkyl radicals, and —N$^+$R$_5$ (X$^-$)$_r$ groups, wherein r is 0 or 1;

K is chosen from a —CH group, —CR groups wherein R is chosen from $C_1$–$C_4$ alkyl radicals and —N$^+$R$_5$(X$^-$)$_r$ groups, wherein r is 0 or 1;

P is chosen from a —CH group, —CR groups, wherein R is chosen from $C_1$–$C_4$ alkyl radicals and —N$^+$R$_5$(X$^-$)$_r$, groups, wherein r is 0 or 1;

$R_5$ is chosen from an O$^-$, $C_1$–$C_4$ alkoxy radicals and $C_1$–$C_4$ alkyl radicals;

$R_6$ and $R_7$, are identical or different and are chosen from a hydrogen atom, a halogen atom chosen from chlorine, bromine, iodine and fluorine, $C_1$–$C_4$ alkyl radicals, $C_1$–$C_4$ alkoxy radicals and —NO$_2$ radicals;

X$^-$ represents an anion;

with the provisos that, if $R_4$ is a $C_1$–$C_4$ alkyl radical and Z is a sulphur atom, then $R_3$ is not a hydrogen atom;

if $R_5$ is O$^-$, then r is zero;

if K or P or M are —N$^+$—$C_1$–$C_4$-alkyl X$^-$, then $R_6$ or $R_7$ is not a hydrogen atom, excepting said cationic direct dyes of formulae ($I_{27}$), ($I_{28}$), ($I_{31}$), ($I_{33}$), ($I_{36}$), ($I_{37}$), $I_{39}$)-($I_{43}$), ($I_{67}$), ($I_{73}$)-($I_{75}$), and ($I_{77}$) below:

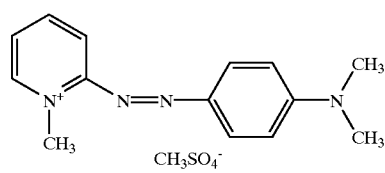
(I)$_{27}$

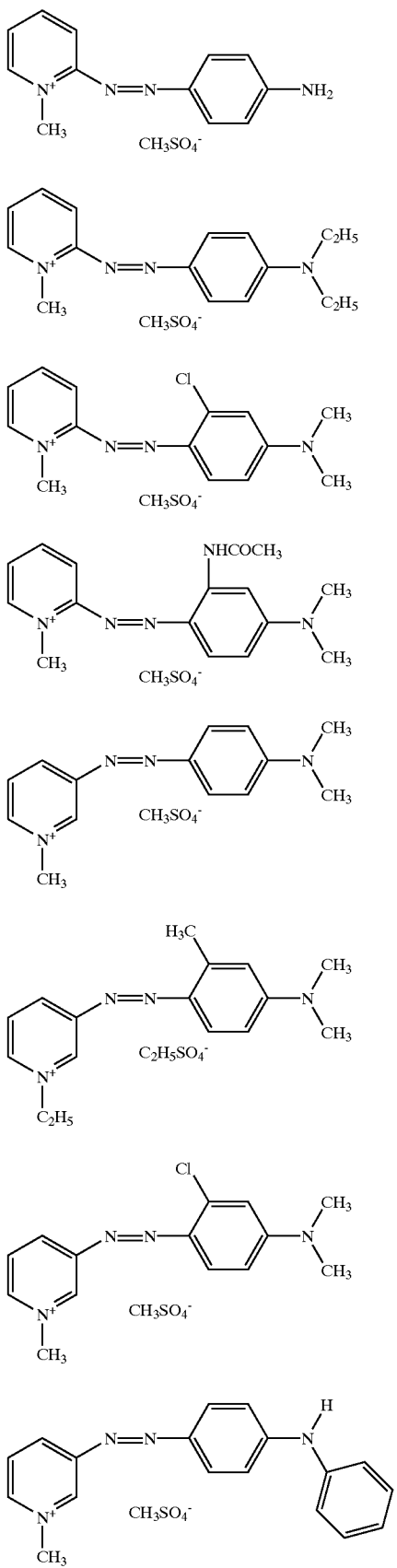
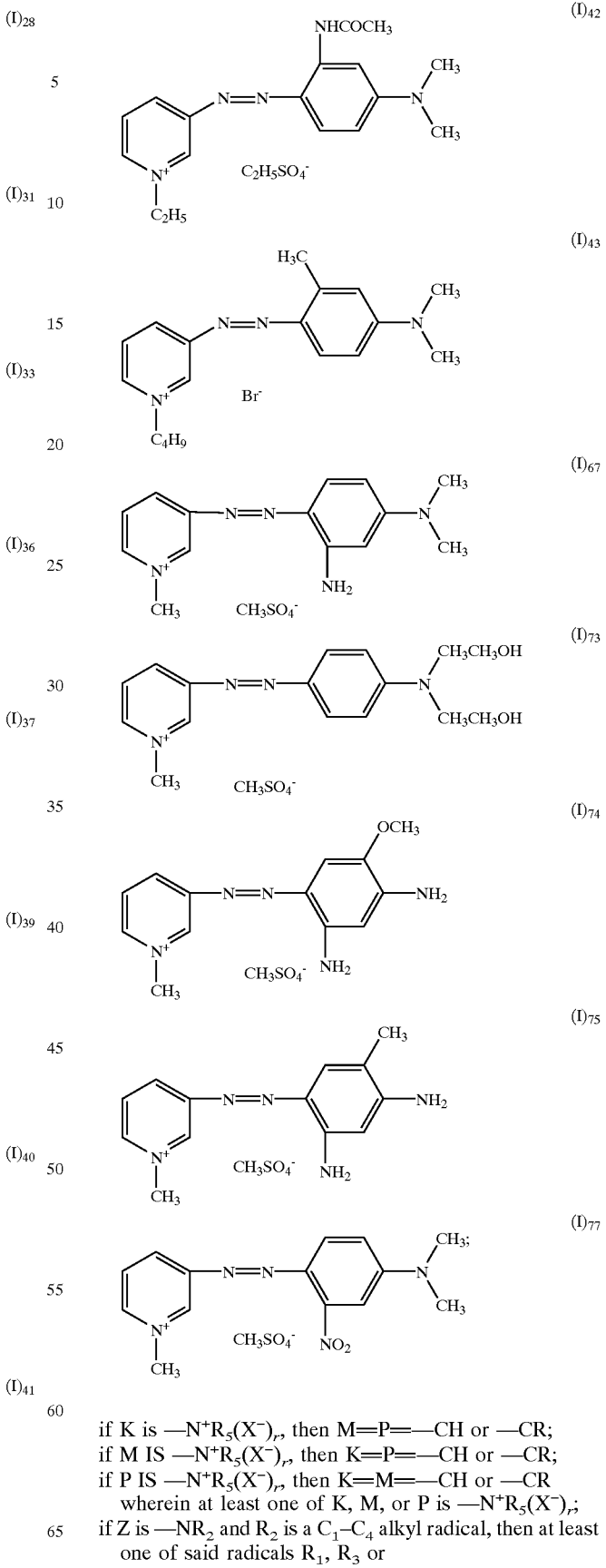
if K is —N⁺R₅(X⁻)ᵣ, then M=P=—CH or —CR;
if M IS —N⁺R₅(X⁻)ᵣ, then K=P=—CH or —CR;
if P IS —N⁺R₅(X⁻)ᵣ, then K=M=—CH or —CR
  wherein at least one of K, M, or P is —N⁺R₅(X⁻)ᵣ;
if Z is —NR₂ and R₂ is a C₁–C₄ alkyl radical, then at least one of said radicals R₁, R₃ or
R₄ on A₂ is not a C₁–C₄ alkyl radical;

the symbol B represents:
(a) a group of structure B1 below:

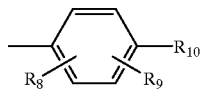

wherein in said structure B1, $R_8$ is chosen from a hydrogen atom, a halogen atom chosen from chlorine, bromine, iodine and fluorine, $C_1$–$C_4$ alkyl radicals, $C_1$–$C_4$ alkoxy radicals, an —OH radical, an —$NO_2$, —$NHR_{11}$ radicals, —$NR_{12}R_{13}$ radicals and —$NHCO(C_1$–$C_4)$alkyl radicals or forms, with $R_9$, a 5- or 6-membered ring which may or may not contain one or more hetero atoms chosen from nitrogen, oxygen and sulphur;

$R_9$ is chosen from a hydrogen atom, a halogen atom chosen from chlorine, bromine, iodine and fluorine, $C_1$–$C_4$ alkyl radicals, and $C_1$–$C_4$ alkoxy radicals, or forms, with $R_{10}$ or $R_{11}$, a 5- or 6-membered ring which may or may not contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, are identical or different and are chosen from $C_1$–$C_4$ alkyl radicals, $C_1$–$C_4$ monohydroxyalkyl radicals and $C_2$–$C_4$ polyhydroxyalkyl radicals; or (b) a 5- or 6-membered nitrogenous heterocyclic group which can contain other hetero atoms and/or carbonyl groups and which is unsubstituted or substituted with at least one radical chosen from $C_1$–$C_4$ alkyl radicals, amino radicals, and phenyl radicals, said second composition comprising, in a medium suitable for dyeing, at least one oxidizing agent, wherein said first composition or said second composition contains at least one polymer chosen from cationic and amphoteric substantive polymers chosen from:

(1) dimethyldiallylammonium halide homopolymers and copolymers;

(2) methacryloyloxyethyltrimethylammonium halide homopolymers and copolymers (3) polyquaternary ammonium polymers chosen from:
polymers comprising repeating units corresponding to formula (II) below:

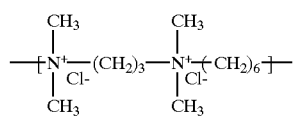

polymers comprising repeating units corresponding to formula (III) below:

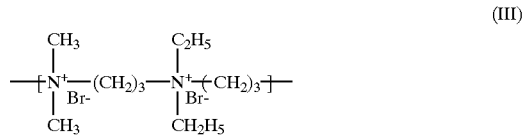

polymers comprising repeating units corresponding to formula (IV) below:

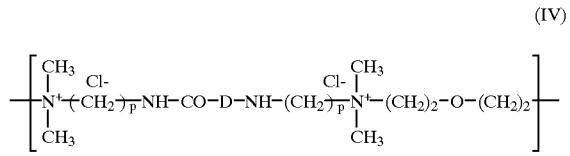

wherein p is chosen from integers ranging from about 1 to about 6,

D is absent or is a —$(CH_2)_r$—CO— group, wherein r represents a number equal to 4 or 7; and (4) vinylpyrrolidone copolymers comprising units chosen from methacrylamidopropyltrimethylammonium units and methylvinylimidazolium units and (ii) applying said mixture of said first composition and said second composition to said keratin fibers for a period of time sufficient to dye said keratin fibers, wherein said mixing occurs before the time of application of said first and second compositions to said keratin fibers.

32. A multi-compartment dyeing device or multi-compartment dyeing kit for dyeing keratin fibers comprising at least two compartments, wherein a first compartment comprises, in a medium suitable for dyeing, at least one oxidation base and at least one cationic direct dye of formula (I) below:

wherein:

the symbol A is chosen from structures A1 to A3 below:

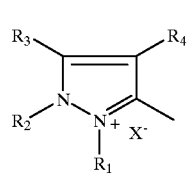

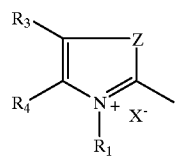

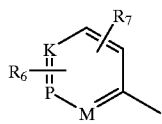

A3 wherein in structures A1 to A3,
$R_1$ is chosen from $C_1$–$C_4$ alkyl radicals and phenyl radicals which are unsubstituted or have a substituent chosen from $C_1$–$C_4$ alkyl radicals and halogen atoms chosen from chlorine, bromine, iodine and fluorine;
$R_2$ is chosen from $C_1$–$C_4$ alkyl radicals and phenyl radicals;
$R_3$ and $R_4$ are identical or different and are chosen from $C_1$–$C_4$ alkyl radicals and phenyl radicals, and
  wherein when said A is said structure A1, can together form a substituted benzene ring, or
  wherein when said A is said structure A2, can together form a benzene ring optionally substituted with at least one radical chosen from $C_1$–$C_4$ alkyl radicals, $C_1$–$C_4$ alkoxy radicals and $NO_2$ radicals;
$R_3$ can also represent a hydrogen atom;
Z is chosen from an oxygen atom, a sulphur atom and —$NR_2$ groups;
M is chosen from a —CH group, —CR groups, wherein R is chosen from $C_1$–$C_4$ alkyl radicals, and —$N^+R_5(X^-)_r$ groups, wherein r is 0 or 1;
K is chosen from a —OH group, —OR groups wherein R is chosen from $C_1$–$C_4$ alkyl radicals and —$N^+R_5(X^-)_r$ groups, wherein r is 0 or 1;
P is chosen from a —CH group, —OR groups, wherein R is chosen from $C_1$–$C_4$ alkyl radicals and —$N^+R_5(X^-)_r$ groups, wherein r is 0 or 1;
$R_5$ is chosen from an $O^-$, $C_1$–$C_4$ alkoxy radicals and $C_1$–$C_4$ alkyl radicals;
$R_6$ and $R_7$, are identical or different and are chosen from a hydrogen atom, a halogen atom chosen from chlorine, bromine, iodine and fluorine, $C_1$–$C_4$ alkyl radicals, $C_1$–$C_4$ alkoxy radicals and —$NO_2$ radicals;
$X^-$ represents an anion;
with the provisos that,
if $R_4$ is a $C_1$–$C_4$ alkyl radical and Z is a sulphur atom, then $R_3$ is not a hydrogen atom;
if $R_5$ is $O^-$, then r is zero;
if K or P or M are —$N^+$—$C_1$–$C_4$-alkyl $X^-$, then $R_6$ or $R_7$ is not a hydrogen atom, excepting said cationic direct dyes of formulae $(I_{27})$, $(I_{28})$, $(I_{31})$, $(I_{33})$, $(I_{36})$, $(I_{37})$, $(I_{39})$–$(I_{43})$, $(I_{67})$, $(I_{73})$–$(I_{75})$, and $(I_{77})$ below:

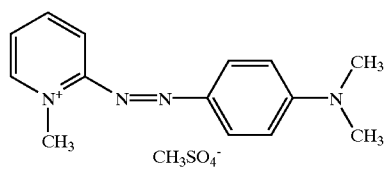
$(I)_{27}$

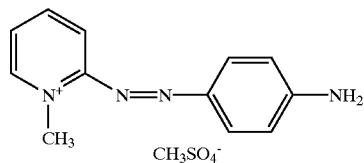
$(I)_{28}$

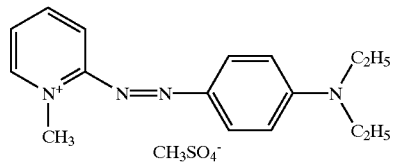
$(I)_{31}$

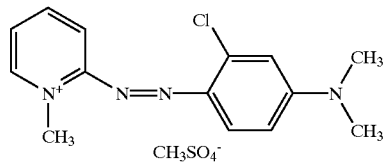
$(I)_{33}$

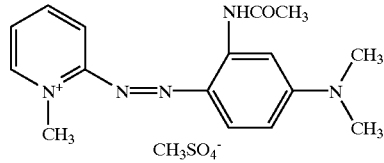
$(I)_{36}$

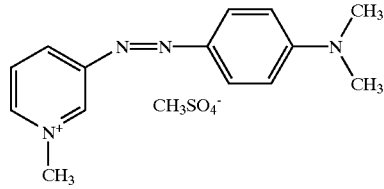
$(I)_{37}$

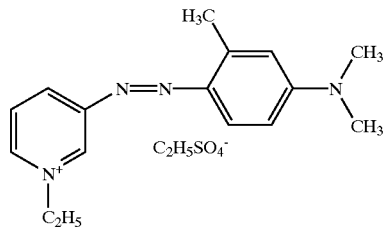
$(I)_{39}$

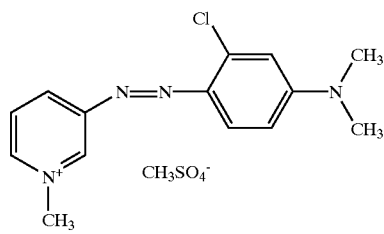
$(I)_{40}$

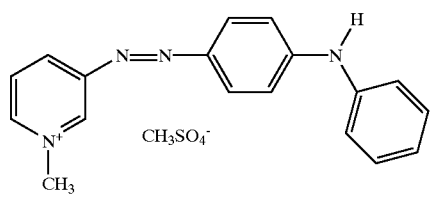
$(I)_{41}$

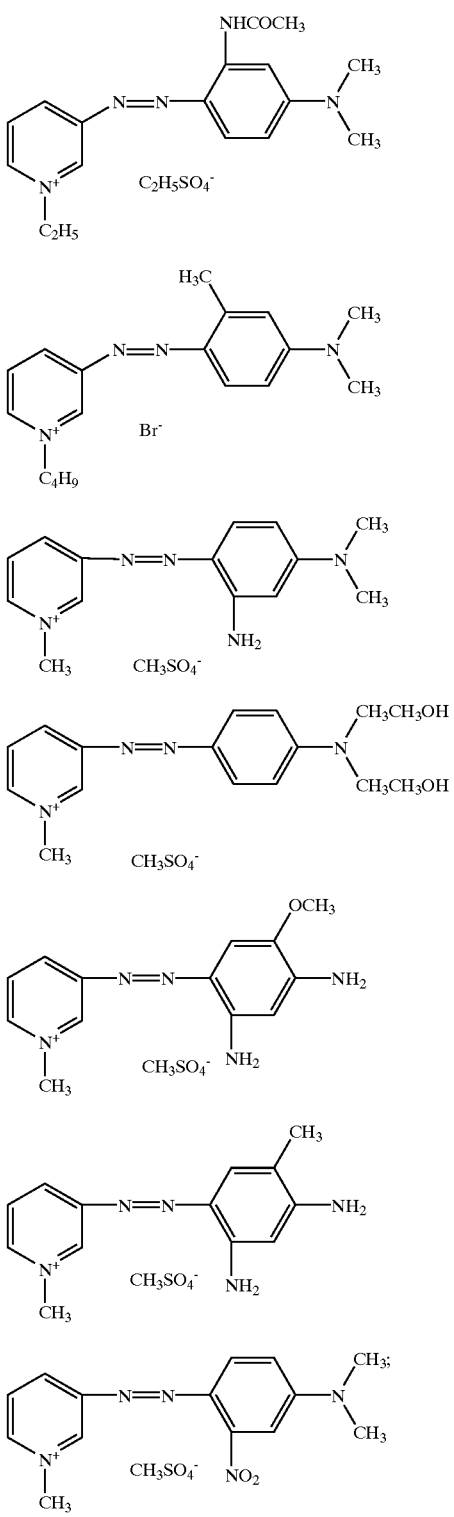

if K is —N⁺R₅(X⁻)ᵣ, then M=P=—CH or —CR;
if M is —N⁺R₅(X⁻)ᵣ, then K=P=—CH or —CR;
If P is —N⁺R₅(X⁻)ᵣ, then K=M=—CH or —CR
 wherein at least one of K, M, or P is —N⁺R₅(X⁻)ᵣ;
if Z is —NR₂ and R₂ is a C₁–C₄ alkyl radical, then at least one of said radicals R₁, R₃ or R₄ on A₂ is not a C₁–C₄ alkyl radical;

the symbol B represents:
 (a) a group of structure B1 below:

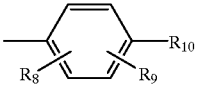

wherein in said structure B1,

R₈ is chosen from a hydrogen atom, a halogen atom chosen from chlorine, bromine, iodine and fluorine, C₁–C₄ alkyl radicals, C₁–C₄ alkoxy radicals, an —OH radical, an —NO₂, —NHR₁₁ radicals, —NR₁₂R₁₃ radicals and —NHCO(C₁–C₄)alkyl radicals or forms, with R₉, a 5- or 6-membered ring which may or may not contain one or more hetero atoms chosen from nitrogen, oxygen and sulphur;

R₉ is chosen from a hydrogen atom, a halogen atom chosen from chlorine, bromine, iodine and fluorine, C₁–C₄ alkyl radicals, and C₁–C₄ alkoxy radicals, or forms, with R₁₀ or R₁₁, a 5- or 6-membered ring which may or may not contain at least one hetero atom chosen from nitrogen, oxygen and sulphur;

R₁₀ is chosen from a hydrogen atom, an —OH radical, —NHR₁₁ radicals and —NR₁₂R₁₃ radicals;

R₁₁ is chosen from a hydrogen atom, C₁–C₄ alkyl radicals, C₁–C₄ monohydroxyalkyl radicals, C₂–C₄ polyhydroxyalkyl radicals and a phenyl radical;

R₁₂ and R₁₃, are identical or different and are chosen from C₁–C₄ alkyl radicals, C₁–C₄ monohydroxyalkyl radicals and C₂–C₄ polyhydroxyalkyl radicals; or (b) a 5- or 6-membered nitrogenous heterocyclic group which can contain other hetero atoms and/or carbonyl groups and which is unsubstituted or substituted with at least one radical chosen from C₁–C₄ alkyl radicals, amino radicals, and phenyl radicals, and a second compartment comprises, in a medium suitable for dyeing, at least one oxidizing agent, wherein said first compartment or said second compartment contains at least one polymer chosen from cationic and amphoteric substantive polymers chosen from:
 (1) dimethyldiallylammonium halide homopolymers and copolymers;
 (2) methacryloyloxyethyltrimethylammonium halide homopolymers and copolymers
 (3) polyquaternary ammonium polymers chosen from:
  polymers comprising repeating units corresponding to formula (II) below:

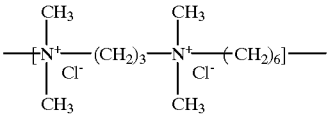

polymers comprising repeating units corresponding to formula (III) below:

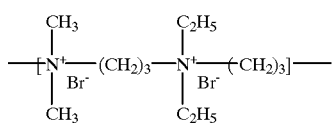
(III)

polymers comprising repeating units corresponding to formula (IV) below:

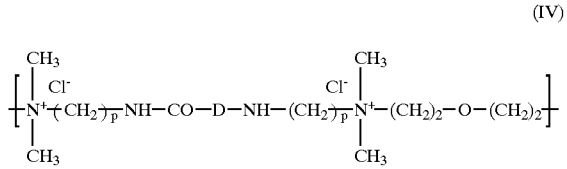
(IV)

wherein p is chosen from integers ranging from about 1 to about 6,
D is absent or is a —(CH$_2$)$_r$—CO— group, wherein r represents a number equal to 4 or 7; and
(4) vinylpyrrolidone copolymers comprising units chosen from methacrylamidopropyltrimethylammonium units and methylvinylimidazolium units.

33. A multi-compartment dyeing device or multi-compartment dyeing kit for dyeing keratin fibers comprising at least two compartments, wherein
a first compartment comprises, in a medium suitable for dyeing, at least one cationic direct dye of formula (I) below:

A—N=N—B    (I)

wherein:
the symbol A is chosen from structures A1 to A3 below:

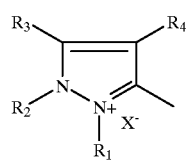
A$_1$

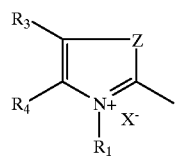
A$_2$

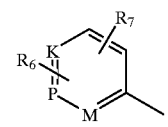
A$_3$ wherein in structures A1 to A3,
R$_1$ is chosen from C$_1$–C$_4$ alkyl radicals and phenyl radicals which are unsubstituted or have a substituent chosen from C$_1$–C$_4$ alkyl radicals and halogen atoms chosen from chlorine, bromine, iodine and fluorine;

R$_2$ is chosen from C$_1$–C$_4$ alkyl radicals and phenyl radicals;

R$_3$ and R$_4$ are identical or different and are chosen from C$_1$–C$_4$ alkyl radicals and phenyl radicals, and
wherein when said A is said structure A1, can together form a substituted benzene ring, or
wherein when said A is said structure A2, can together form a benzene ring optionally substituted with at least one radical chosen from C$_1$–C$_4$ alkyl radicals, C$_1$–C$_4$alkoxy radicals and NO$_2$ radicals;

R$_3$ can also represent a hydrogen atom;

Z is chosen from an oxygen atom, a sulphur atom and —NR$_2$ groups;

M is chosen from a —CH group, —CR groups, wherein R is chosen from C$_1$–C$_4$ alkyl radicals, and —N$^+$R$_5$(X$^-$)$_r$ groups, wherein r is 0 or 1;

K is chosen from a —CH group, —CR groups wherein R is chosen from C$_1$–C$_4$ alkyl radicals and —N$^+$R$_5$(X$^-$)$_r$ groups, wherein r is 0 or 1;

P is chosen from a —CH group, —CR groups, wherein R is chosen from C$_1$–C$_4$ alkyl radicals and —N$^+$R$_5$(X$^-$)$_r$ groups, wherein r is 0 or 1;

R$_5$ is chosen from an O$^-$, C$_1$–C$_4$ alkoxy radicals and C$_1$–C$_4$ alkyl radicals;

R$_6$ and R$_7$, are identical or different and are chosen from a hydrogen atom, a halogen atom chosen from chlorine, bromine, iodine and fluorine, C$_1$–C$_4$ alkyl radicals, C$_1$–C$_4$ alkoxy radicals and —NO$_2$ radicals;

X represents an anion;

with the provisos that,
if R$_4$ is a C$_1$–C$_4$ alkyl radical and Z is a sulphur atom, then R$_3$ is not a hydrogen atom;
if R$_5$ is O$^-$, then r is zero;
if K or P or M are —N$^+$—C$_1$–C$_4$-alkyl X, then R$_6$ or R$_7$ is not a hydrogen atom, excepting said cationic direct dyes of formulae (I$_{27}$), (I$_{28}$), (I$_{31}$), (I$_{33}$), (I$_{36}$), (I$_{37}$), (I$_{39}$)–(I$_{43}$), (I$_{67}$), (I$_{73}$)–(I$_{75}$), and (I$_{77}$) below:

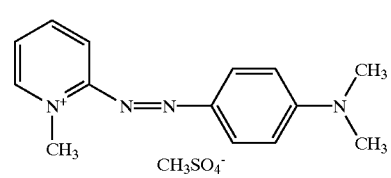
(I)$_{27}$

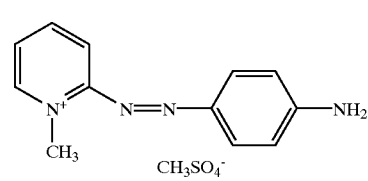
(I)$_{28}$

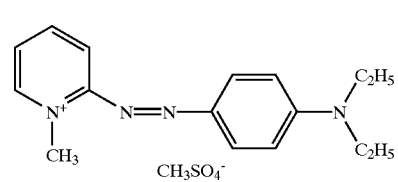
(I)$_{31}$

-continued (I)₃₃ 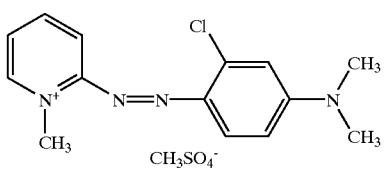

(I)₃₆ 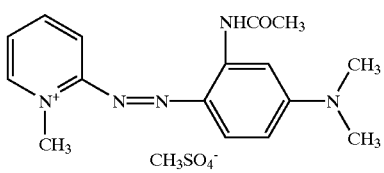

(I)₃₇ 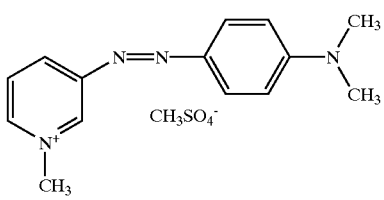

(I)₃₉ 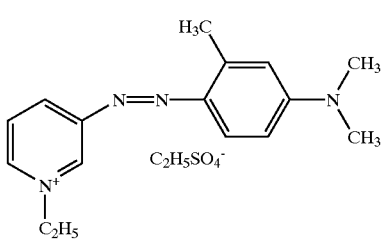

(I)₄₀ 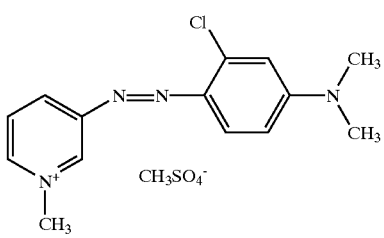

(I)₄₁ 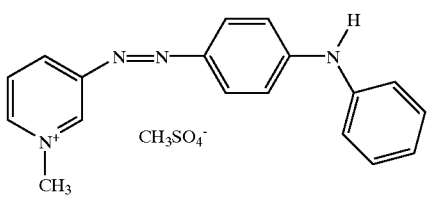

(I)₄₂ 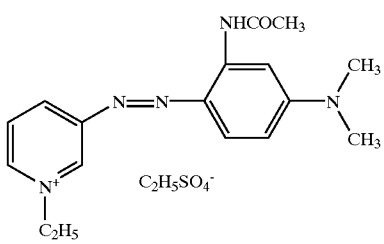

(I)₄₃ 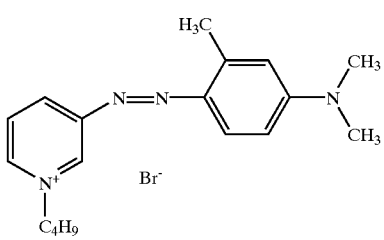

-continued (I)₆₇ 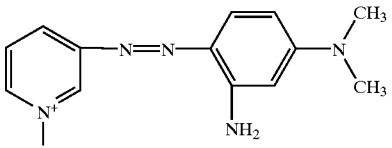

(I)₇₃ 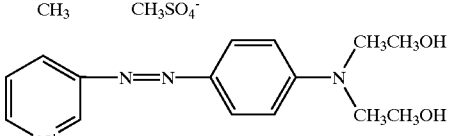

(I)₇₄ 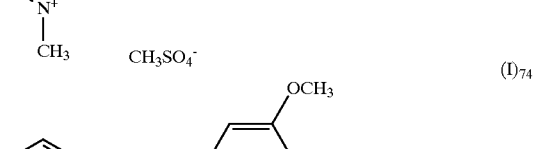

(I)₇₅ 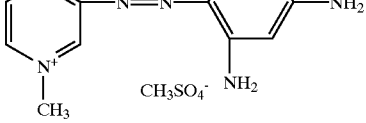

(I)₇₇ 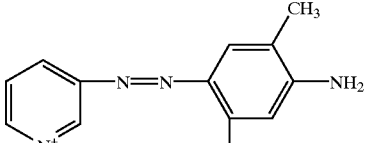

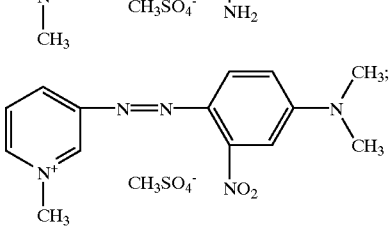

if K IS —N⁺R₅(X⁻)ᵣ, then M=P=—CH or —CR;
if M is —N⁺R₅(X⁻)ᵣ, then K=P=—CH or —CR;
if P is —N⁺R₅(X⁻)ᵣ, then K=M=—CH or —CR
   wherein at least one of K, M, or P is —N⁺R₅(X⁻)ᵣ;
if Z is —NR₂ and R₂ is a C₁–C₄ alkyl radical, then at least one of said radicals R₁, R₃ or R₄ on A₂ is not a C₁–C₄ alkyl radical;
the symbol B represents:
   (a) a group of structure B1 below:

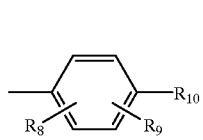 B₁ wherein in said structure B1,
   R₈ is chosen from a hydrogen atom, a halogen atom chosen from chlorine, bromine, iodine and fluorine, C₁–C₄ alkyl radicals, C₁–C₄ alkoxy radicals, an —OH radical, an —NO₂, —NHR₁₁ radicals, —NR₁₂R₁₃ radicals and —NHCO(C₁–C₄)alkyl radicals or forms, with R₉, a 5- or 6-membered ring which may or may not contain one or more hetero atoms chosen from nitrogen, oxygen and sulphur;
   R₉ is chosen from a hydrogen atom, a halogen atom chosen from chlorine, bromine, iodine and fluorine, $C_1$–$C_4$ alkyl radicals, and $C_1$–$C_4$ alkoxy radicals, or forms, with $R_{10}$ or $R_{11}$, a 5- or 6-membered ring which may or may not contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, are identical or different and are chosen from $C_1$–$C_4$ alkyl radicals, $C_1$–$C_4$ monohydroxyalkyl radicals and $C_2$–$C_4$ polyhydroxyalkyl radicals; or (b) a 5- or 6-membered nitrogenous heterocyclic group which can contain other hetero atoms and/or carbonyl groups and which is unsubstituted or substituted with at least one radical chosen from $C_1$–$C_4$ alkyl radicals, amino radicals, and phenyl radicals, and a second compartment comprises, in a medium suitable for dyeing, at least one oxidizing agent, wherein said first compartment or said second compartment contains at least one polymer chosen from cationic and amphoteric substantive polymers chosen from:

(1) dimethyldiallylammonium halide homopolymers and copolymers;

(2) methacryloylethyltrimethylammonium halide homopolymers and copolymers (3) polyquaternary ammonium polymers chosen from: polymers comprising repeating units corresponding to formula (II) below:

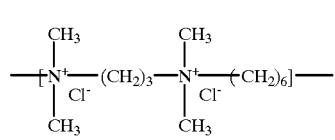

(II)

polymers comprising repeating units corresponding to formula (III) below:

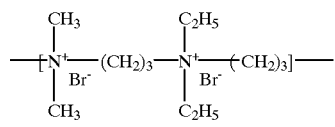

(III)

polymers comprising repeating units corresponding to formula (IV) below:

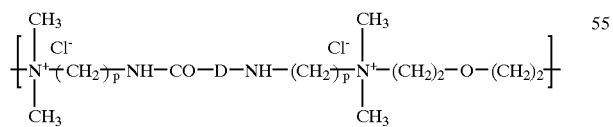

(IV)

wherein p is chosen from integers ranging from about 1 to about 6,

D is absent or is a —$(CH_2)_r$—CO— group, wherein r represents a number equal to 4 or 7; and (4) vinylpyrrolidone copolymers comprising units chosen from methacrylamidopropylammonium units and methylvinylimidazolium units.

34. A composition in the form of a liquid, a shampoo, a cream, or a gel, wherein said composition comprises:

(i) at least one cationic direct dye chosen from cationic direct dyes of structures $(I)_1$ to $(I)_{77}$ below:

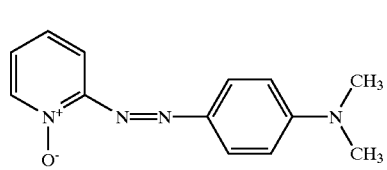

$(I)_1$

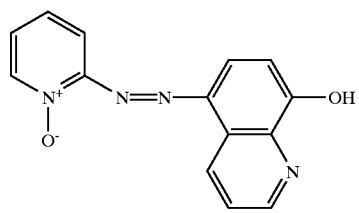

$(I)_2$

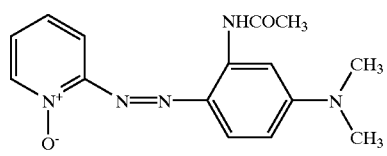

$(I)_3$

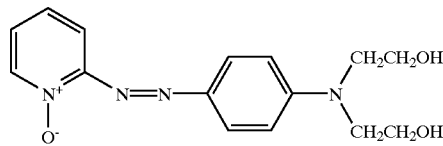

$(I)_4$

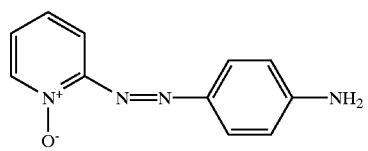

$(I)_5$

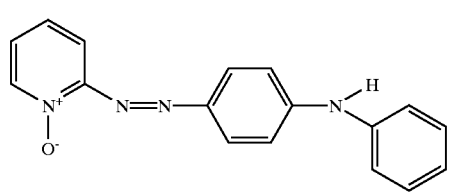

$(I)_6$

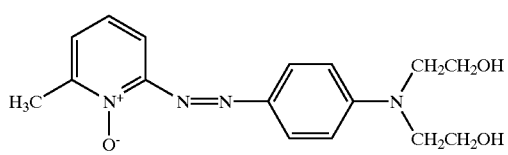

$(I)_7$

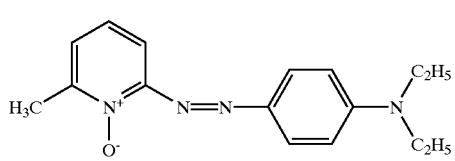

$(I)_8$

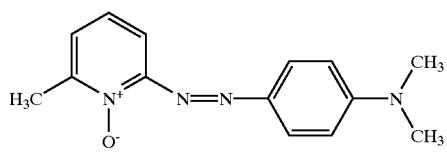(I)9
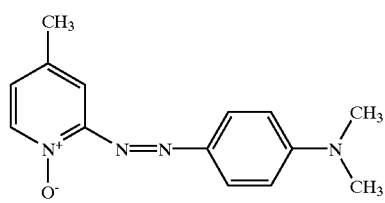(I)10
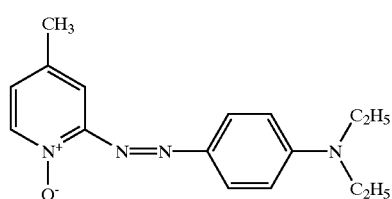(I)11
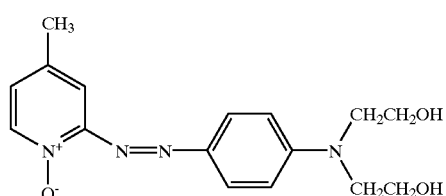(I)12
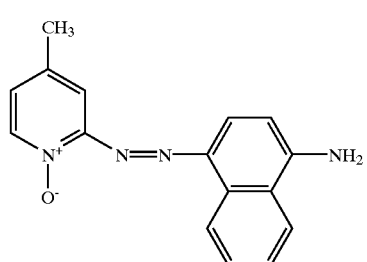(I)13
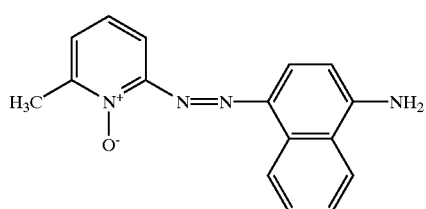(I)14
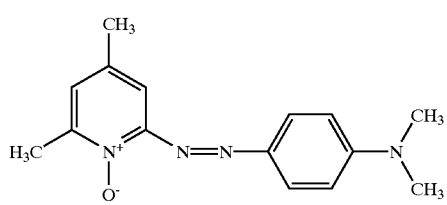(I)15
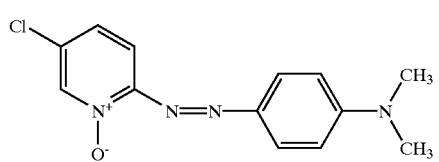(I)16
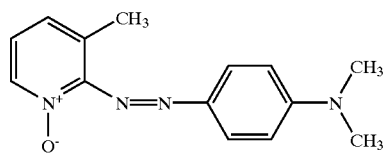(I)17
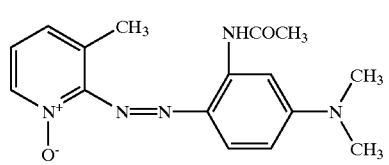(I)18
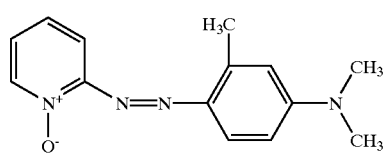(I)19
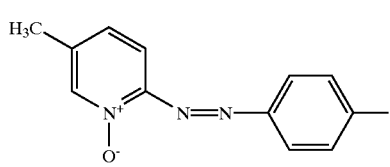(I)20
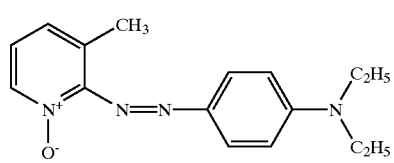(I)21
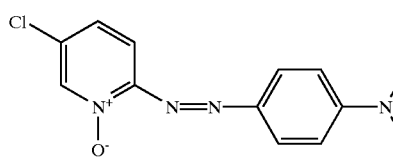(I)22
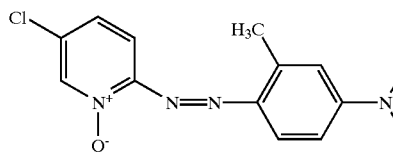(I)23
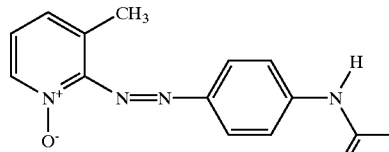(I)24
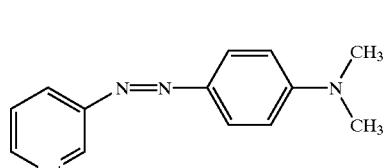(I)25

-continued
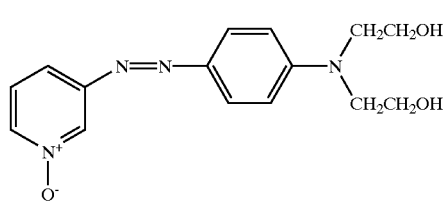
(I)26
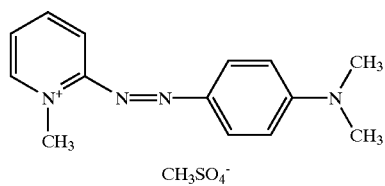
(I)27
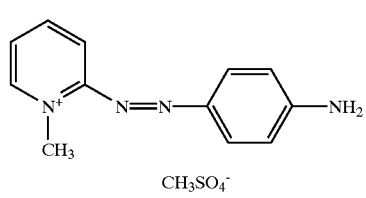
(I)28
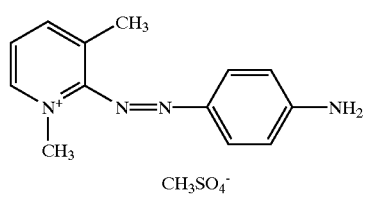
(I)29
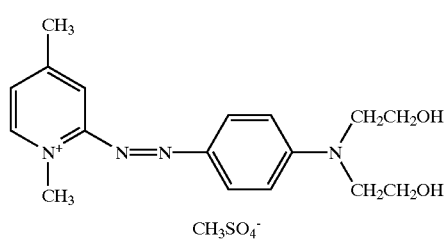
(I)30
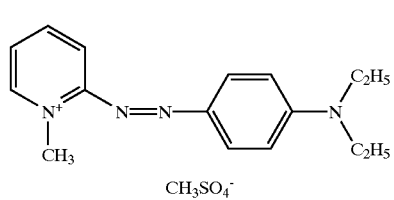
(I)31
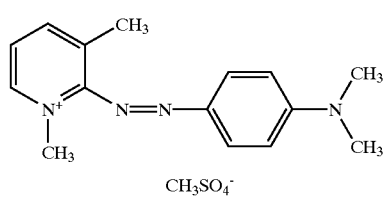
(I)32
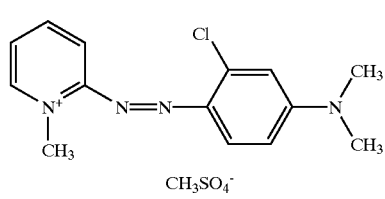
(I)33
-continued
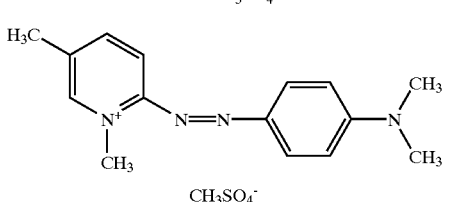
(I)34
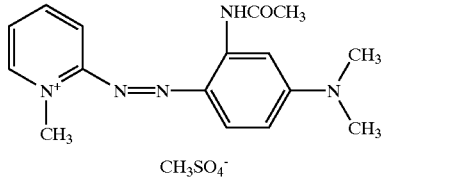
(I)35
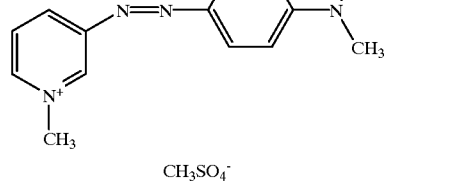
(I)36
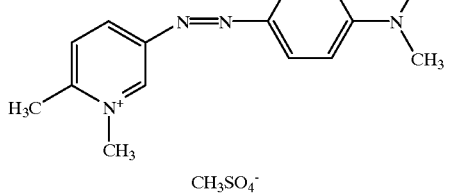
(I)37
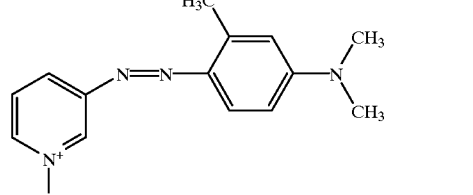
(I)38
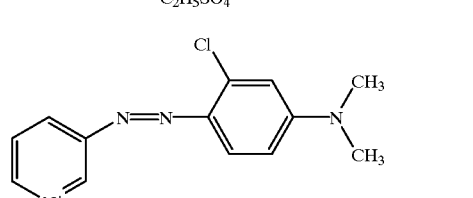
(I)39
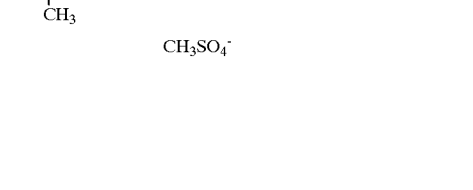
(I)40

-continued (I)₄₁: 3-[(4-anilinophenyl)azo]-1-methylpyridinium methylsulfate (I)₄₂: 3-[(2-acetamido-4-dimethylaminophenyl)azo]-1-ethylpyridinium ethylsulfate (I)₄₃: 1-butyl-3-[(4-dimethylamino-2-methylphenyl)azo]pyridinium bromide (I)₄₄: 2-[(3-methyl-5-oxo-1-phenyl-4,5-dihydro-1H-pyrazol-4-yl)azo]-1-methoxypyridinium methylsulfate (I)₄₅: 2-[(2,4,6-trioxohexahydropyrimidin-5-yl)azo]pyridine 1-oxide (I)₄₆: 2-[(4-dimethylaminophenyl)azo]-3-methylbenzothiazolium perchlorate (I)₄₇: 2-[(4-dimethylaminophenyl)azo]-1,3-dimethylbenzimidazolium perchlorate (I)₄₈: 2-[(2,6-diamino-3-pyridyl)azo]pyridine 1-oxide (I)₄₉: 2-[(2,4-diamino-5-methylphenyl)azo]-3-methylbenzothiazolium iodide (I)₅₀: 2-[(6-hydroxy-3,4-dihydro-2H-1,4-benzoxazin-7-yl)azo]-4-methyl-3-phenylthiazolium perchlorate (I)₅₁: 2-[(6-hydroxy-3,4-dihydro-2H-1,4-benzoxazin-7-yl)azo]-3-methylbenzothiazolium chloride (I)₅₂: 2-[(6-hydroxy-3,4-dihydro-2H-1,4-benzoxazin-7-yl)azo]-3,4-diphenylthiazolium perchlorate (I)₅₃: 2-[(2,4-diamino-5-methoxyphenyl)azo]pyridine 1-oxide (I)₅₄: 2-[(5-acetamido-2-hydroxy-4-methylphenyl)azo]pyridine 1-oxide -continued (I)₅₅ — chemical structure (I)₅₆ — chemical structure (I)₅₇ — chemical structure (I)₅₈ — chemical structure (I)₅₉ — chemical structure (I)₆₀ — chemical structure (I)₆₁ — chemical structure (I)₆₂ — chemical structure (I)₆₃ — chemical structure (I)₆₄ — chemical structure (I)₆₅ — chemical structure (I)₆₆ — chemical structure (I)₆₇ — chemical structure (I)₆₈ — chemical structure (I)₆₉ — chemical structure (I)₇₀ — chemical structure (I)₇₁ 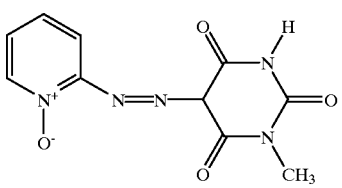

(I)₇₂ 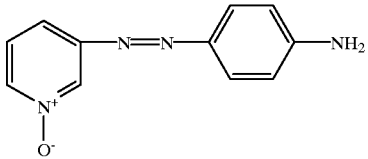

(I)₇₃ 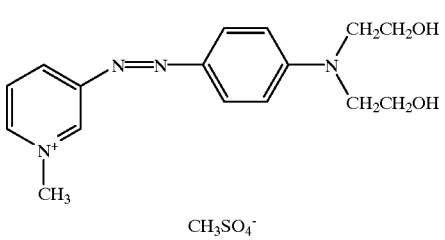

(I)₇₄ 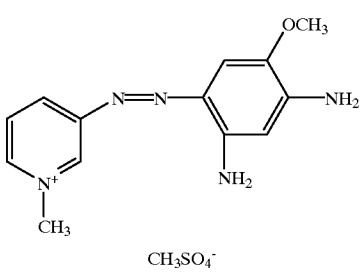

(I)₇₅ 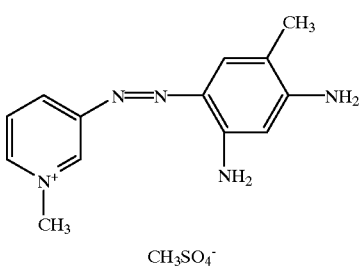

(I)₇₆ 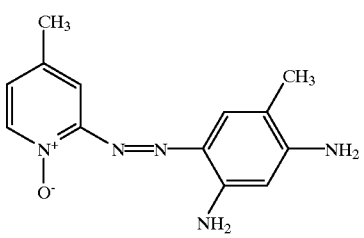

(I)₇₇ 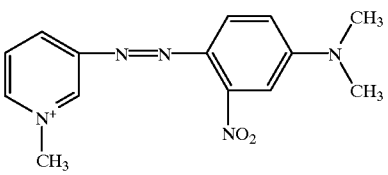

and (ii) at lese one polymer chosen from cationic and amphoteric substantive polymers chosen from:
(1) dimethyldiallylammonium halide homopolymers and copolymers;
(2) methacryloyloxyethyltrimethlammonium halide homopolymers and copolymers
(3) polyquaternary ammonium polymers chosen from: polymers comprising repeating units corresponding to formula (II) below:

(II) 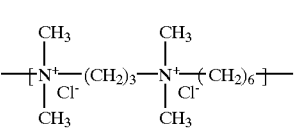

polymers comprising repeating units corresponding to formula (III)

(III) 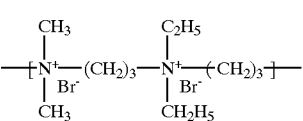

polymers comprising repeating units corresponding to formula (IV) below:

(IV) 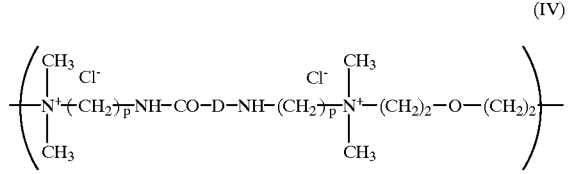

wherein p is chosen from integers ranging from about 1 to about 6,

D is absent or is a —(CH₂)ᵣ—CO— group, wherein r represents a number equal to 4 or 7; and
(4) vinylpyrrolidone copolymers comprising units chosen from methacrylamidopropyltrimethylammonium units and methylvinylimidazolium units.

* * * * *

UNITED STATES PATENT AND TRADEMARK OFFICE
CERTIFICATE OF CORRECTION

PATENT NO. : 6,592,633 B2                                     Page 1 of 3
DATED     : May 25, 1999
INVENTOR(S) : Gérard Lang et al.

It is certified that error appears in the above-identified patent and that said Letters Patent is hereby corrected as shown below:

Column 30,
Line 41, "-(CH$_2$)$_r$CO-" should read -- -(CH$_2$)$_r$-CO- --.

Column 31,
Line 24, "out" should read -- about --.

Column 43,
Line 40, "C$_1$-C$_4$alkoxy" should read -- C$_1$-C$_4$ alkoxy --.
Line 45, "-OH group, -OR groups," should read -- -CH group, -CR groups, --.
Line 46, "N$^+$R$_5$(X$^-$)$_r$" should read -- -N$^+$R$_5$(X$^-$)$_r$ --.
Line 49, "-N$^-$R$_5$(X$^-$)$_r$" should read -- -N$^+$R$_5$(X$^-$)$_r$ --.
Line 64, "atom" should read -- atom; --.

Column 43,
Lines 33-39, in structure "(I)$_{73}$,

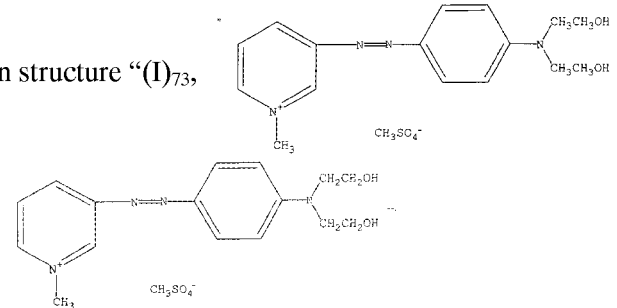

should read

Column 46,
Line 28, "R$_{10}$or" should read -- R$_{10}$ or --.
Line 38, "C$_1$-C$_4$monohydroxyalkyl" should read -- C$_1$-C$_4$ monohydroxyalkyl --.
Lines 50-51, "contain" should read -- contains --.

Column 48,
Line 26, "C$_1$-C$_4$alkoxy" should read -- C$_1$-C$_4$ alkoxy --.
Line 31, "-OH group, -OR groups," should read -- CH group, -CR groups, --.
Line 40, "-N$^+$R$_5$(X$^-$)$_r$," should read -- -N$^+$R$_5$(X$^-$)$_r$ --.
Line 58, "I$_{39}$)-(I$_{43}$)," should read -- (I$_{39}$)-(I$_{43}$), --.

Column 50,
Lines 29-34, in strucute (I)$_{73}$,

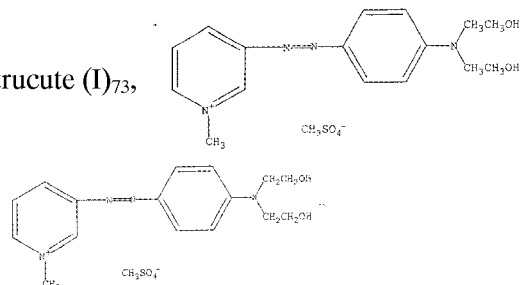

should read

UNITED STATES PATENT AND TRADEMARK OFFICE
CERTIFICATE OF CORRECTION

PATENT NO.    : 6,592,633 B2
DATED         : May 25, 1999
INVENTOR(S)   : Gérard Lang et al.

It is certified that error appears in the above-identified patent and that said Letters Patent is hereby corrected as shown below:

Column 50 (cont'd),
Lines 62 and 63, "IS" should read -- is --.

Column 53,
Line 26, "$C_1$-$C_4$alkoxy" should read -- $C_1$-$C_4$ alkoxy --.
Line 35, "-OH group, -OR groups," should read -- -CH group, -CR groups, --.
Line 39, "-OR" should read -- -CR --.

Column 55,
Lines 28-34, in structure $(I)_{73}$, 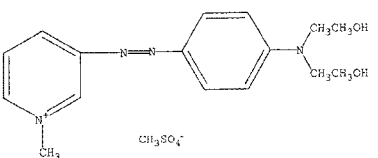

should read 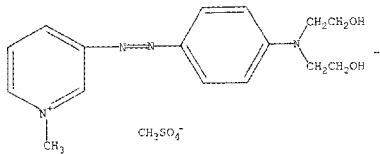

Column 57,
Lines 4-9, in strucute (III), 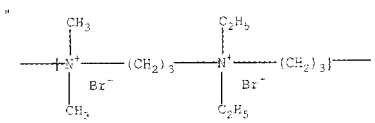

should read 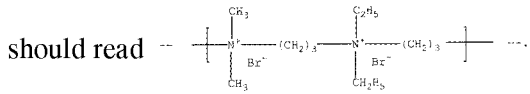

Column 58,
Line 11, "$C_1$-$C_4$alkoxy" should read -- $C_1$-$C_4$ alkoxy --.
Line 34, "X" should read -- $X^-$ --.
Line 41, "X," should read -- $X^-$ --.

Column 60,
Lines 9-14, in structure $(I)_{73}$, 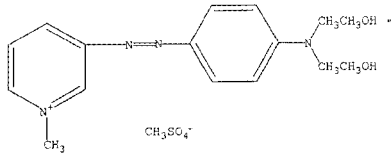

should read 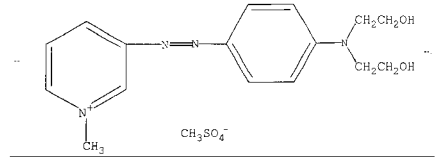

Line 40, "IS" should read -- is --.

UNITED STATES PATENT AND TRADEMARK OFFICE
CERTIFICATE OF CORRECTION

PATENT NO. : 6,592,633 B2
DATED : May 25, 1999
INVENTOR(S) : Gérard Lang et al.

It is certified that error appears in the above-identified patent and that said Letters Patent is hereby corrected as shown below:

Column 61,
Lines 43-48, in formula (III), " 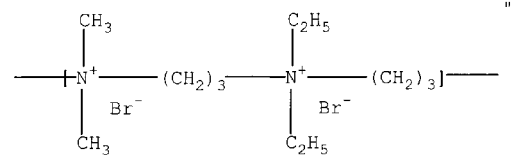 "

should read 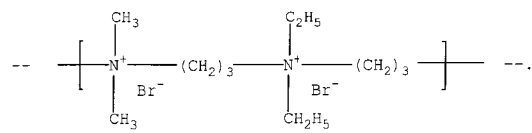 --.

Column 72,
Line 14, "lese" should read -- least --.
Line 18, "methacryloyloxyethyltrimethlammonium" should read
-- methacryloyloxyethyltrimethylammonium --.
Line 32, "formula (III)" should read -- formula (III) below: --.

Lines 44-50, in formula (IV), " 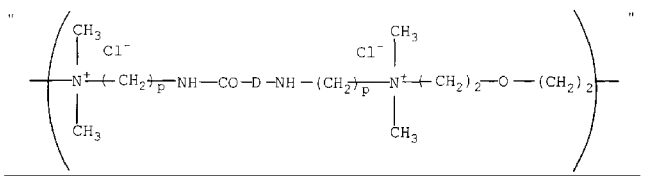 "

should read 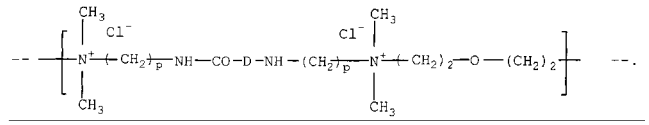 --.

Signed and Sealed this

Twenty-first Day of September, 2004

JON W. DUDAS
*Director of the United States Patent and Trademark Office*

UNITED STATES PATENT AND TRADEMARK OFFICE
CERTIFICATE OF CORRECTION

PATENT NO.   : 6,592,633 B2                                               Page 1 of 3
DATED        : May 25, 1999
INVENTOR(S)  : Gérard Lang et al.

It is certified that error appears in the above-identified patent and that said Letters Patent is hereby corrected as shown below:

Column 30,
Line 41, "-(CH$_2$)$_r$CO-" should read -- -(CH$_2$)$_r$-CO- --.

Column 31,
Line 24, "out" should read -- about --.

Column 43,
Line 40, "C$_1$-C$_4$alkoxy" should read -- C$_1$-C$_4$ alkoxy --.
Line 45, "-OH group, -OR groups," should read -- -CH group, -CR groups, --.
Line 46, "N$^+$R$_5$(X$^-$)$_r$" should read -- -N$^+$R$_5$(X$^-$)$_r$ --.
Line 49, "-N$^-$R$_5$(X$^-$)$_r$" should read -- -N$^+$R$_5$(X$^-$)$_r$ --.
Line 64, "atom" should read -- atom; --.

Column 43,
Lines 33-39, in structure "(I)$_{73}$, should read

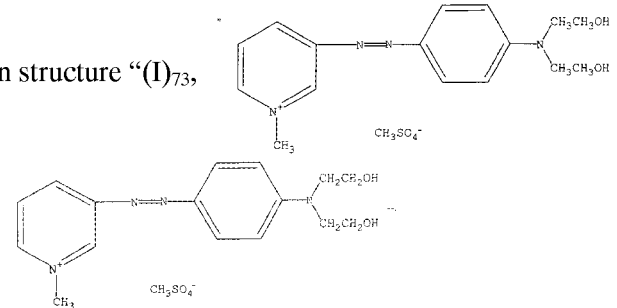

Column 46,
Line 28, "R$_{10}$or" should read -- R$_{10}$ or --.
Line 38, "C$_1$-C$_4$monohydroxyalkyl" should read -- C$_1$-C$_4$ monohydroxyalkyl --.
Lines 50-51, "contain" should read -- contains --.

Column 48,
Line 26, "C$_1$-C$_4$alkoxy" should read -- C$_1$-C$_4$ alkoxy --.
Line 31, "-OH group, -OR groups," should read -- CH group, -CR groups, --.
Line 40, "-N$^+$R$_5$(X$^-$)$_r$," should read -- -N$^+$R$_5$(X$^-$)$_r$ --.
Line 58, "I$_{39}$)-(I$_{43}$)," should read -- (I$_{39}$)-(I$_{43}$), --.

Column 50,
Lines 29-34, in strucute (I)$_{73}$, should read

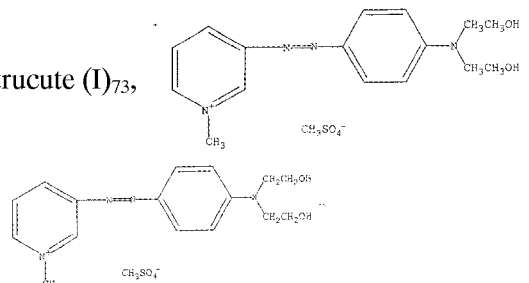

UNITED STATES PATENT AND TRADEMARK OFFICE
CERTIFICATE OF CORRECTION

PATENT NO. : 6,592,633 B2
DATED : May 25, 1999
INVENTOR(S) : Gérard Lang et al.

It is certified that error appears in the above-identified patent and that said Letters Patent is hereby corrected as shown below:

Column 50 (cont'd),
Lines 62 and 63, "IS" should read -- is --.

Column 53,
Line 26, "$C_1$-$C_4$alkoxy" should read -- $C_1$-$C_4$ alkoxy --.
Line 35, "-OH group, -OR groups," should read -- -CH group, -CR groups, --.
Line 39, "-OR" should read -- -CR --.

Column 55,
Lines 28-34, in structure (I)$_{73}$,

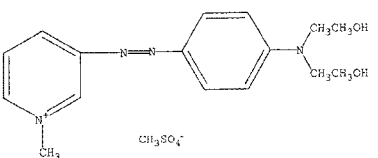

should read 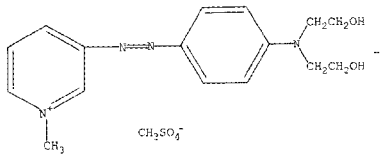

Column 57,
Lines 4-9, in strucute (III),

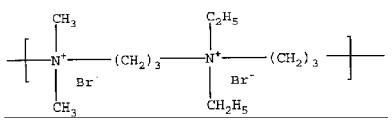

should read 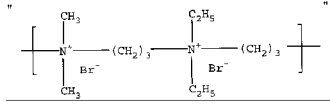

Column 58,
Line 11, "$C_1$-$C_4$alkoxy" should read -- $C_1$-$C_4$ alkoxy --.
Line 34, "X" should read -- X$^-$ --.
Line 41, "X," should read -- X$^-$ --.

Column 60,
Lines 9-14, in structure (I)$_{73}$,

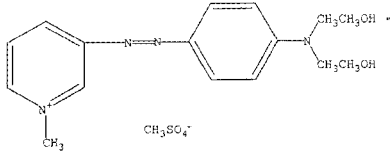

should read 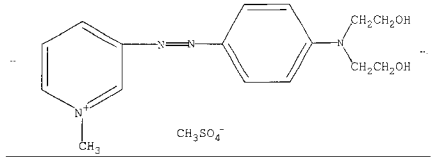

Line 40, "IS" should read -- is --.

UNITED STATES PATENT AND TRADEMARK OFFICE
CERTIFICATE OF CORRECTION

PATENT NO. : 6,592,633 B2
DATED : May 25, 1999
INVENTOR(S) : Gérard Lang et al.

It is certified that error appears in the above-identified patent and that said Letters Patent is hereby corrected as shown below:

Column 61,
Lines 43-48, in formula (III), 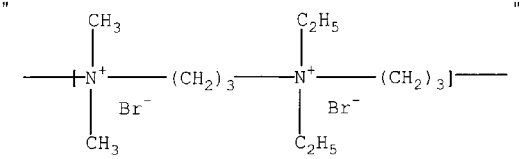

should read 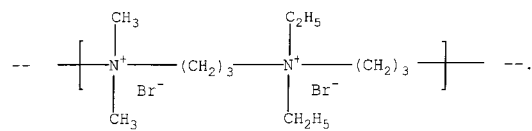

Column 72,
Line 14, "lese" should read -- least --.
Line 18, "methacryloyloxyethyltrimethlammonium" should read
-- methacryloyloxyethyltrimethylammonium --.
Line 32, "formula (III)" should read -- formula (III) below: --.

Lines 44-50, in formula (IV), 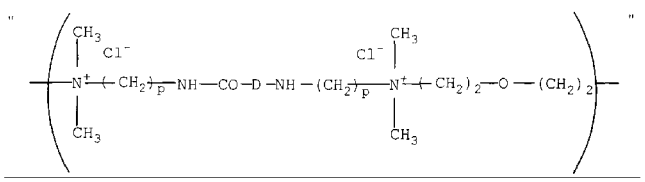

should read 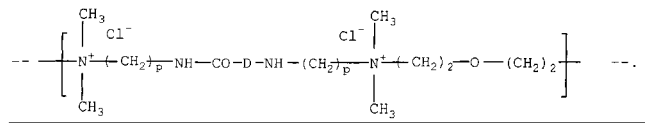

Signed and Sealed this

Thirtieth Day of November, 2004

JON W. DUDAS
*Director of the United States Patent and Trademark Office*